(12) United States Patent
Qin et al.

(10) Patent No.: US 12,306,361 B2
(45) Date of Patent: May 20, 2025

(54) X-RAY DIAGNOSTIC APPARATUS AND MEDICAL IMAGE PROCESSING APPARATUS

(71) Applicant: Canon Medical Systems Corporation, Otawara (JP)

(72) Inventors: Yuling Qin, Nasushiobara (JP); Ping Xin, Yokohama (JP); Yukiko Tomooka, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 319 days.

(21) Appl. No.: 17/929,837

(22) Filed: Sep. 6, 2022

(65) Prior Publication Data
US 2023/0072986 A1 Mar. 9, 2023

(30) Foreign Application Priority Data
Sep. 9, 2021 (JP) .................... 2021-146837

(51) Int. Cl.
*G01T 7/00* (2006.01)
*A61B 6/58* (2024.01)
*G06T 11/00* (2006.01)

(52) U.S. Cl.
CPC .............. *G01T 7/005* (2013.01); *A61B 6/584* (2013.01); *A61B 6/585* (2013.01); *G06T 11/005* (2013.01)

(58) Field of Classification Search
CPC ........ A61B 6/584; A61B 6/585; A61B 6/4441; G01T 7/005
See application file for complete search history.

(56) References Cited

U.S. PATENT DOCUMENTS 5,442,674 A 8/1995 Picard et al.
6,466,638 B1 10/2002 Silver et al.

FOREIGN PATENT DOCUMENTS

JP 2005021675 A * 1/2005 ............. A61B 6/466
JP 2013-000273 A 1/2013

* cited by examiner

*Primary Examiner* — Dani Fox
*Assistant Examiner* — Casey Bryant
(74) *Attorney, Agent, or Firm* — Oblon, McClelland, Maier & Neustadt, L.L.P.

(57) ABSTRACT

According to one embodiment, an X-ray diagnostic apparatus includes processing circuitry. The processing circuitry is configured to execute first calculation processing of calculating three-dimensional position information of each of an X-ray generator and an X-ray detector during rotation imaging, based on projection data acquired by executing the rotation imaging for a phantom with the X-ray generator and the X-ray detector arranged rotatably around the phantom.

16 Claims, 12 Drawing Sheets

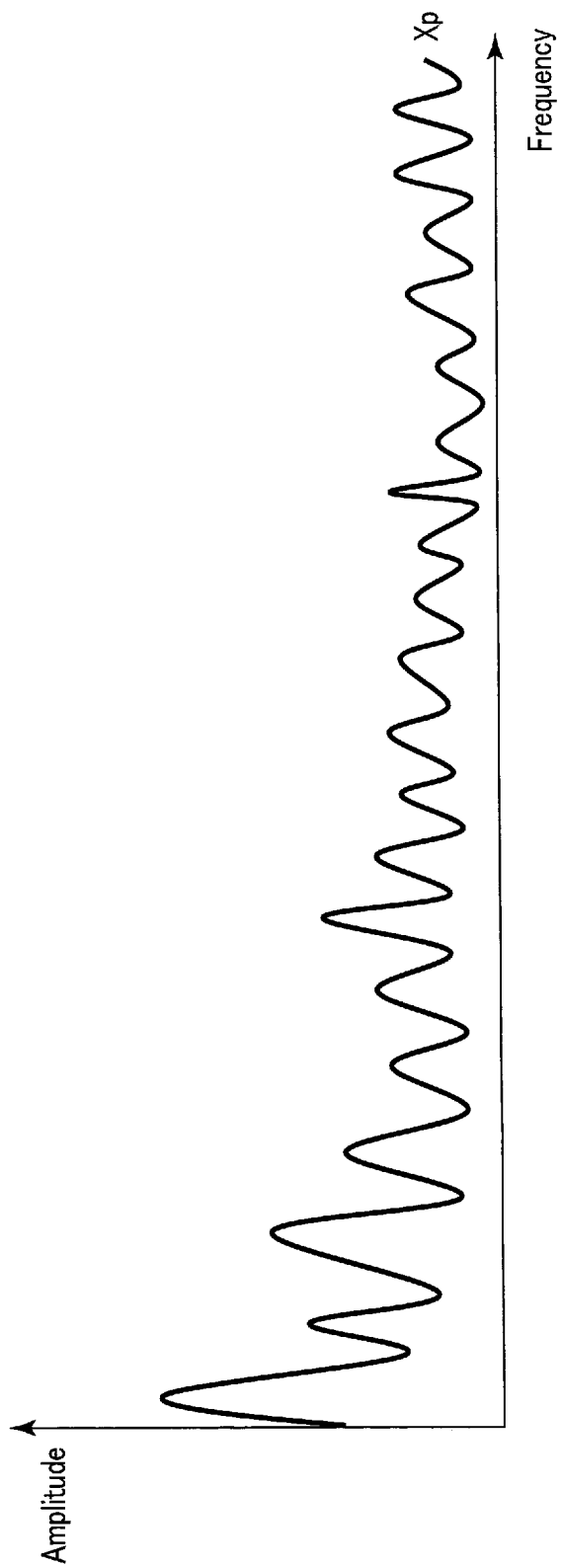
F I G. 10

X-RAY DIAGNOSTIC APPARATUS AND MEDICAL IMAGE PROCESSING APPARATUS

CROSS-REFERENCE TO RELATED APPLICATION

This application is based upon and claims the benefit of priority from prior Japanese Patent Application No. 2021-146837, filed Sep. 9, 2021, the entire contents of which are incorporated herein by reference.

FIELD

Embodiments described herein relate generally to an X-ray diagnostic apparatus and a medical image processing apparatus.

BACKGROUND

A technique of detecting a difference (artifact) from the actual shape of the imaged phantom with a reconstructed image of CT by an X-ray diagnostic apparatus is known. In the technique, a projection image is reconstructed by executing rotation imaging for a phantom to calculate characteristic values of artifact of the reconstructed image. A mechanical state of the X-ray diagnostic apparatus can be diagnosed by associating the characteristic values with a malfunction database prepared in advance.

Such a technique has no problems in an ordinary state but, according to study by the inventor(s), has room for improvement in that the mechanical state of the X-ray diagnostic apparatus cannot be diagnosed until any artifact occurs in the reconstructed image.

BRIEF DESCRIPTION OF THE DRAWINGS

FIG. 10 is a schematic diagram for explaining a frequency spectrum relating to oscillation of the X-ray focal point acquired from FIG. 8.

DETAILED DESCRIPTION

Figure 1:
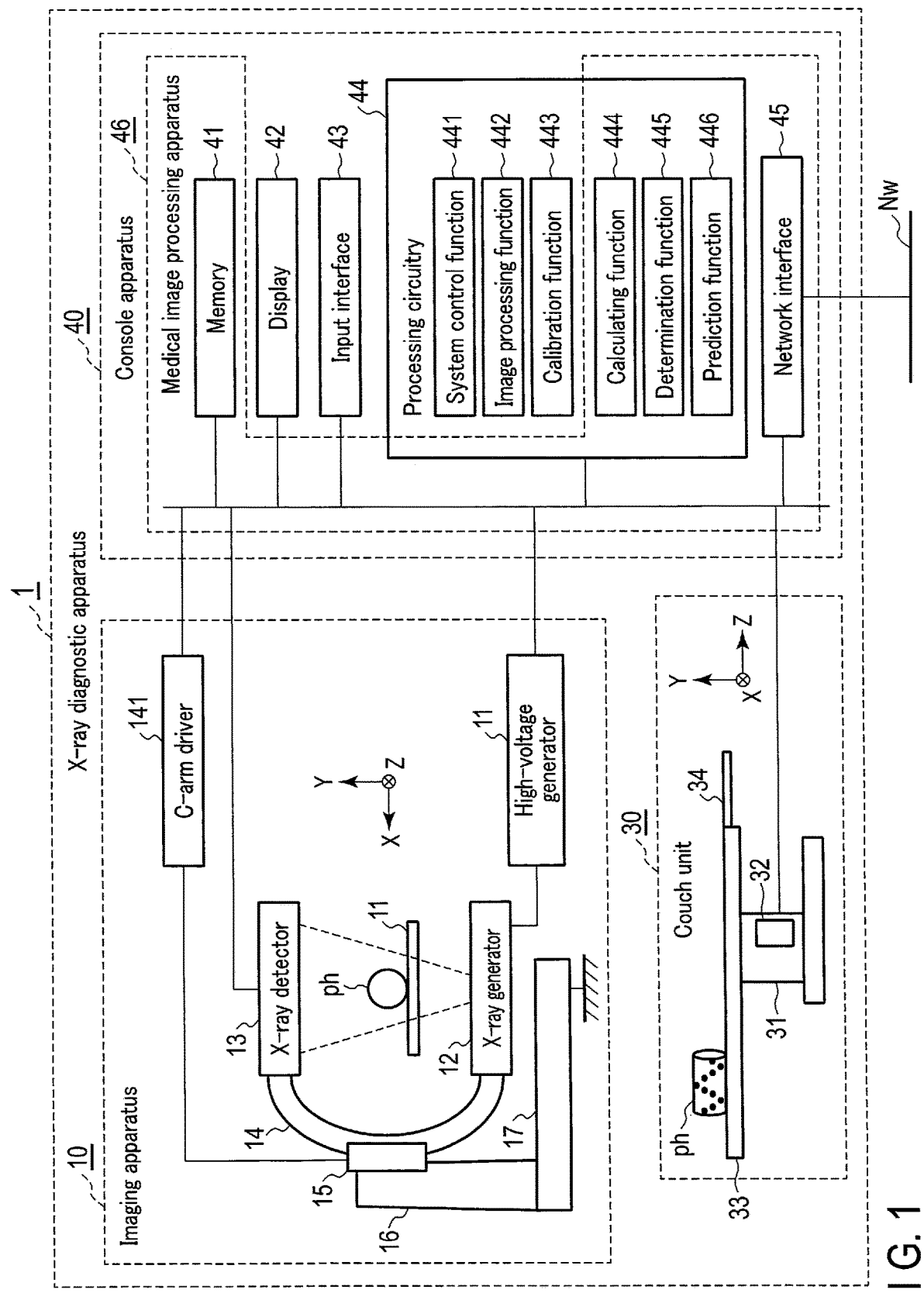
FIG. 1 is a block diagram showing configuration of an X-ray diagnostic apparatus according to a first embodiment.

According to one embodiment, an X-ray diagnostic apparatus includes processing circuitry. The processing circuitry is configured to execute first calculation processing of calculating three-dimensional position information of each of an X-ray generator and an X-ray detector during rotation imaging, based on projection data acquired by executing the rotation imaging for a phantom with the X-ray generator and the X-ray detector arranged rotatably around the phantom.

Embodiments will now be explained hereinafter with reference to drawings. In each of the embodiments, constituent elements similar to those in the preceding drawings are denoted by the same reference numerals and a detailed explanation thereof will be omitted, and different constituent elements will be mainly explained.

First Embodiment

Figure 2:
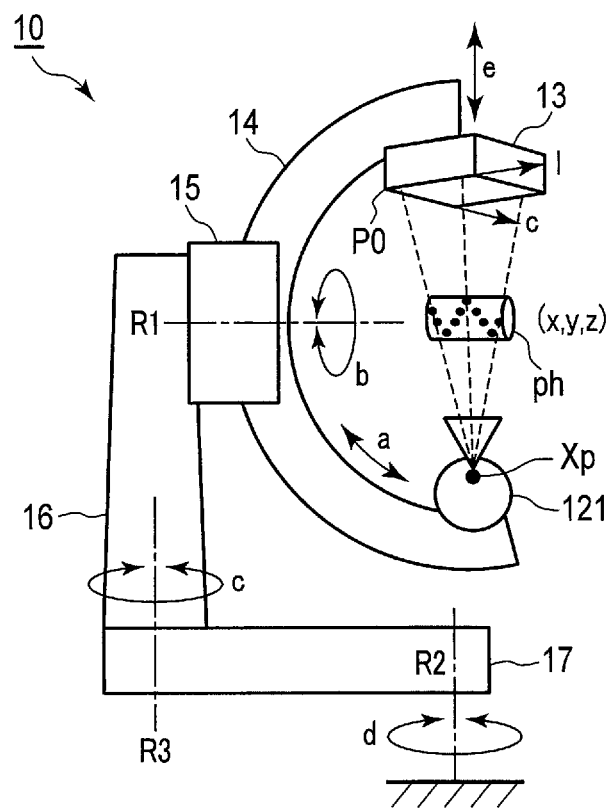
FIG. 2 is a schematic diagram for explaining configuration of part of the X-ray diagnostic apparatus according to the first embodiment.

FIG. 1 is a block diagram showing configuration of an X-ray diagnostic apparatus according to a first embodiment, and FIG. 2 is a schematic diagram for explaining configuration of part of the X-ray diagnostic apparatus. The following explanation illustrates an X-ray diagnostic apparatus 1 for circulatory organs using a C-arm of a floor type, but the structure is not limited thereto. For example, the X-ray diagnostic apparatus may be an X-ray diagnostic apparatus using a C-arm or an Q-arm of a ceiling suspension type. In addition, the following explanation illustrates the case where the target of rotation imaging is a phantom ph, but a patient (subject) serves as the target of rotation imaging in X-ray inspection for a patient.

Specifically, for example, the X-ray diagnostic apparatus 1 includes an imaging apparatus 10, a couch unit 30, and a console apparatus 40. The imaging apparatus 10 includes a high-voltage generator 11, an X-ray generator 12, an X-ray detector 13, a C-arm 14, a C-arm driver 141, a holder 15, a stand 16, and a floor turning arm 17.

The high-voltage generator 11 generates high voltage to be applied between an anode and a cathode to accelerate thermal electrons generated from the cathode of an X-ray tube, and outputs the high voltage to the X-ray tube.

The X-ray generator 12 generates X-rays. Specifically, the X-ray generator 12 includes an X-ray tube 121 applying X-rays to a phantom ph, and an X-ray collimator having a function of limiting the X-ray irradiation field and/or attenuating X-rays for part of the irradiation field.

The X-ray tube 121 generates X-rays. Specifically, the X-ray tube 121 is a vacuum tube retaining a cathode generating thermal electrons and an anode receiving the thermal electrons flying from the cathode. Examples of the X-ray tube 121 include an X-ray tube of a rotating anode type generating X-rays by applying thermal electrons to the rotating anode. The X-ray tube 121 is connected to the high-voltage generator 11 via a high-voltage cable. A tube voltage is applied between the cathode and the anode with the high-voltage generator 11. By application of the tube voltage, thermal electrons fly from the cathode to the anode. A tube current flows with thermal electrons flying from the cathode to the anode. By application of the high voltage from the high-voltage generator 11 and supply of a filament current, thermal electrons fly from the cathode to the anode, and X-rays are generated by collision of the thermal electrons against the anode.

The X-ray collimator is disposed between the X-ray tube and the X-ray detector 13, and generally includes a collimator blade, an added filter, and a compensating filter. The X-ray collimator narrows the X-rays generated with the X-ray tube to be applied only to a region of interest of the phantom ph by blocking X-rays other than the aperture region. For example, the X-ray collimator includes four collimator blades formed of four lead plates, and adjusts the region in which X-rays are blocked to a desired size by sliding the collimator blades. The collimator blades of the X-ray collimator is driven with a driving device (not illustrated) in accordance with the region of interest input by the operator via the input interface 43. An added filter to adjust the total filtration for X-rays can be inserted in the X-ray collimator through a slit. A lead mask and/or a compensating filter used in X-ray inspection can be inserted in the X-ray collimator through an accessary insertion port. The compensating filter may include a ROI (Region Of Interest) filter having a function of attenuating or reducing the amount of X-ray radiation.

The X-ray detector 13 detects X-rays transmitted through the phantom ph. As the X-ray detector 13, it is possible to use a detector directly converting X-rays into electric charges or a detector converting X-rays into light and thereafter converting the light into electric charges. The example herein illustrates the former, but the detector may be the latter. Specifically, the X-ray detector 13 includes a planar FPD (Flat Panel Detector) converting X-rays transmitted through the phantom ph into electric charges and storing the electric charges, and a gate driver generating a driving pulse to read the electric charges stored in the FPD. The FPD is formed of minute detection elements arranged in a column direction and a line direction in a two-dimensional manner. Each of the detection elements includes a photoelectric film detecting X-rays and generating electric charges in accordance with the amount of incident X-rays, a charge storage capacitor storing the electric charges generated in the photoelectric film, and a TFT (thin-film transistor) outputting the electric charges stored in the charge storage capacitor at a certain timing. The stored electric charges are successively read with the driving pulse supplied from the gate driver.

A projection data generation circuit and a projection data storage circuit (not illustrated) are provided at the subsequent stage of the X-ray detector 13. The projection data generation circuit includes a charge-voltage converter converting the electric charges read in parallel in rows or columns into the voltage, an A/D converter converting the output of the charge-voltage converter into a digital signal, and a parallel-serial converter converting the digital parallel signal into a time-series serial signal. The projection data generation circuit supplies the serial signal as time-series projection data to the projection data storage circuit. The projection data storage circuit successively stores the time-series projection data supplied from the projection data generation circuit, and generates two-dimensional projection data (X-ray image). In other words, the X-ray detector 13 detects the X-rays transmitted through the phantom ph and successively generates an X-ray image. The X-ray image (two-dimensional projection data) is stored in a memory 41.

The C-arm 14 retains the X-ray generator 12 and the X-ray detector 13 such that they opposed to each other with the phantom ph and a couch top 33 interposed therebetween, to execute X-ray imaging for the phantom ph on the couch top 33. The C-arm 14 enables execution of rotation imaging for the phantom ph with the X-ray generator 12 and the X-ray detector arranged to be rotatable around the phantom ph.

Specifically, the C-arm 14 is held with the holder 15 rotatably around an axis of an X direction orthogonal to both of a Y direction perpendicular to the couch top 33 and a Z direction extending along the longitudinal direction of the couch top 33. In addition, the C-arm 14 has a substantially arc shape with a Z-direction axis serving as the center, and is held with the holder 15 slidably along the substantially arc shape. Specifically, the C-arm 14 is slidable with the Z-direction axis serving as the rotation center. The C-arm 14 is also capable of making a rotating motion (hereinafter referred to as "main rotating motion") around the holder 15 with an X-direction axis serving as the center, and enables observation with an X-ray image at various angles and in various directions by combinations of the slide and the rotation. The C-arm 14 is also capable of rotating around a Y-direction axis, and enables setting the rotation center axis of the sliding motion described above to the X direction. An imaging axis extending through a focal point Xp of the X-ray tube 121 and a detection surface center of the X-ray detector 13 is designed to cross the rotation center axis of the sliding motion and the rotation center axis of the main rotating motion at a point. The intersection point is generally referred to as "isocenter". The isocenter is not displaced even when the C-arm 14 makes the sliding motion and/or the main rotating motion described above. For this reason, in a case where the region of interest is positioned in the isocenter, the region of interest can be easily observed in a moving image of a medical image acquired by the sliding motion or the main rotating motion of the C-arm 14.

The C-arm 14 is provided in a proper part corresponding to a plurality of power sources to achieve such a sliding motion and a rotating motion. These power sources form the C-arm driver 141. The C-arm driver 141 reads a driving signal from a system control function 441, and causes the C-arm 4 to make a sliding motion, a rotating motion, and/or a linear motion. The C-arm 14 is also provided with a state detector (not illustrated) detecting information of an angle, an attitude, and/or a position thereof.

As illustrated in FIG. 2 in detail, the C-arm 14 is held on the stand 16 via the holder 15, and the C-arm 14 is attached to a side surface of the holder 15 slidably in a direction of an arrow a. By contrast, the holder 15 is attached to the stand 16 rotatably in a direction of an arrow b around a motion axis R1 orthogonal to a longitudinal direction of the stand 16. With rotation of the holder 15, the C-arm 14 is also rotated around the X axis. The X-ray detector 13 is attached to an end portion of the C-arm 14 slidably in an e direction. The X-ray detector 13 can be set to a desired position and direction with respect to the phantom ph placed on the couch top 33, by rotation of the holder 15 in the b direction and sliding of the X-ray detector 13 in the e direction.

By contrast, one end portion of the floor turning arm 17 placed on the floor surface is attached to the floor surface rotatably around a motion axis R2. The stand 16 is attached to the other end portion of the floor turning arm 17 around a motion axis R3. In this case, each of the motion axis R2 of the floor turning arm 17 and the motion axis R3 of the stand 16 is set in the Y direction.

Specifically, the standard positions of the X-ray generator 12 and the X-ray detector 13 are uniquely determined by the following items (i) to (v): (i) the sliding moving distance of the C-arm 14 in the a direction; (ii) the rotation angle of the holder 15 in the b direction; (iii) the rotation angle of the floor turning arm 17 in the d direction; (iv) the rotation angle of the stand 16 in the c direction; and (v) the sliding moving distance of the X-ray detector 13 in the e direction. The locus of the standard position continuously changed may be referred to as "standard locus position". Such a standard locus position may be used for processing of calculating motion state data indicating a deviation from three-dimensional position information described later.

For this reason, a plurality of power sources are provided to form the C-arm driver 141 to move or rotate the C-arm 14, the holder 15, the stand 16, and the floor turning arm 17 in certain directions. Examples of the power sources include a C-arm sliding mechanism unit sliding the C-arm 14, a holder rotating mechanism unit rotating the holder 15 in the b direction, a stand rotating mechanism unit rotating the stand 16 in the c direction, a floor turning arm rotating mechanism unit rotating the floor turning arm 17 in the d direction, and an imaging system sliding mechanism unit sliding the X-ray detector 13 in the e direction. Each of the C-arm sliding mechanism unit, the holder rotating mechanism unit, the stand rotating mechanism unit, the floor turning arm rotating mechanism unit, and the imaging system sliding mechanism unit includes a bearing rotatably coupling a plurality of members or a sliding unit slidably coupling the members. The bearing and/or the sliding unit form a coupling portion. If such a coupling portion rattles, oscillation appears in motion state data indicating a deviation of the standard locus position from the three-dimensional position information described below.

With reference to FIG. 1 again, the couch unit 30 is an apparatus to place and move the phantom ph, and includes a base 31, a couch driver 32, the couch top 33, and a support frame 34.

The base 31 is a housing placed on the floor surface and supporting the support frame 34 movably in a vertical direction (Y direction).

The couch driver 32 is a motor or an actuator contained in the housing of the couch unit 30 and moving the couch top 33 on which the phantom ph is placed in the longitudinal direction (Z direction) of the couch top 33. The couch driver 32 reads a driving signal from the system control function 441, and moves the couch top 33 in the horizontal direction and/or the vertical direction with respect to the floor surface. Movement of the C-arm or the couch top 33 changes the positional relation of the imaging axis with respect to the phantom ph. The couch driver 32 may move the support frame 34 in the longitudinal direction of the couch top 33, in addition to the couch top 33.

The couch top 33 is a plate provided on an upper surface of the support frame 34 and on which the phantom ph is placed.

The support frame 34 is provided on an upper part of the base 31 and supports the couch top 33 slidably in the longitudinal direction thereof.

The console apparatus 40 includes a memory 41, a display 42, an input interface 43, processing circuitry 44, and a network interface 45.

The memory 41 includes a memory main member recording electrical information, such as a ROM (Read Only Memory), a RAM (Random Access Memory), a HDD (Hardware Disk Drive), and an image memory, and a peripheral circuit, such as a memory controller and a memory interface, accompanying the memory main member. The memory 41 stores, for example, a program executed with the processing circuitry 44, X-ray images generated with the processing circuitry 44, data used for processing with the processing circuitry 44, data being processed, and processed data. The data includes calibration data and/or projection data described later. The memory 41 is an example of a storage unit.

The display 42 is formed of a display main member displaying a medical image and the like, an internal circuit supplying a display signal to the display main member, and a peripheral circuit, such as a connector and/or a cable connecting the display main member and the internal circuit. The internal circuit generates display data by superimposing supplementary information, such as subject information and projection data generating conditions, on the image data supplied from the processing circuitry 44, executes D/A conversion and TV format conversion for the acquired display data, and displays the display data on the display main member.

The input interface 43 executes input of various types of information, setting of X-ray imaging conditions including the X-ray application condition, and input of various command signals. The input interface 43 is achieved with, for example, a track ball to issue an moving instruction for the C-arm 14 and/or set a region of interest (ROI), a switch button, a mouse, a keyboard, a touch pad to execute an input operation by touch on an operating surface thereof, and a touch panel display in which a display screen and a touch pad are integrated. The input interface 43 is connected to the processing circuitry 44, converts an input operation received from the operator into an electrical signal, and outputs the signal to the processing circuitry 44. In the present specification, the input interface 43 is not limited to elements including a physical operating component, such as a keyboard. For example, examples of the input interface 43 also include an electrical signal processing circuit receiving an electrical signal corresponding to an input operation from an external input device provided separately from the apparatus and outputting the electrical signal to the processing circuitry 44.

The processing circuitry 44 is a processor calling and executing a program in the memory 41 to achieve a system control function 441, an image processing function 442, a calibration function 443, a calculating function 444, a determination function 445, and a prediction function 446 corresponding to the program. Examples of the program of this type include a mechanical state detection program to cause the computer (medical image processing apparatus 46) to achieve the calculating function 444. The mechanical state detection program may cause the computer to further achieve the determination function 445, the prediction function 446, and the image processing function 442, if necessary. Distribution of the functions, such as the calculating function 444, the determination function 445, and the prediction function 446, is an example and is not specifically limited. For example, the calculating function 444 may bear part of the determination function 445 or the prediction function 446. In the same manner, the determination function 445 may bear part of the calculating function 444 or the prediction function 446. Also in the same manner, the prediction function 446 may bear part of the calculating function 444 or the determination function 445. In addition, FIG. 1 illustrates that the single processing circuitry 44 achieves the system control function 441, the image processing function 442, the calibration function 443, the calculating function 444, the determination function 445, and the prediction function 446, but a plurality of independent processors may be combined to form the processing circuit, and the functions may be achieved by executing the program with the processors. The system control function 441, the image processing function 442, the calibration function 443, the calculating function 444, the determination function 445, and the prediction function 446 may be referred to as "system control circuit", "image processing circuit", "calibration circuit", "calculating circuit", "determination circuit", and "prediction circuit", respectively, and may be mounted as individual hardware circuits. The processing circuitry 44 is an example of a first calculating unit, a second calculating unit, a third calculating unit, a fourth calculating unit, a first determination unit, a second determination unit, a third determination unit, and a prediction unit.

The system control function 441 temporarily stores, for example, a command signal input by the operator from the input interface 43 and information, such as various initial setting conditions, and transmits the information to each of processing functions of the processing circuitry 44. The system control function 441 also controls the C-arm driver 141 and the couch driver 32 using, for example, information relating to driving of the C-arm 14 and/or the couch top 33 input from the input interface 43. The system control function also reads the stored information, such as the various initial setting conditions, and controls the X-ray application conditions, such as the tube current, the tube voltage, and the application time in the high-voltage generator 11.

The image processing function 442 may store, for example, X-ray images (projection data) successively generated with the X-ray detector 13 in the memory 41. The image processing function 442 may execute ordinary image processing, such as noise reduction and background compression, for the X-ray images stored in the memory 41. The image processing function 442 also reads a signal from the system control function 441 or the like, and executes control to acquire a desired X-ray image from the memory 41 and display the X-ray image on the display 42. The image processing function 442 also displays the X-ray image having been subjected to image processing on the display 42.

The calibration function 443 is a function to execute a calibration method for an X-ray path of the X-ray diagnostic apparatus 1. The calibration function 443 calculates calibration data, and stores the calibration data in the memory 41. For example, as illustrated in FIG. 2, X-rays emitted from the focal point Xp of the X-ray tube 121 passes through the phantom ph, and reaches the detector surface of the X-ray detector 13. In this manner, correlation is calculated between the position of a specific point on the phantom ph and the position of the detector surface on which the specific point is projected. The correlation is referred to as "calibration data". The calibration data may also be referred to as "wobble table". U.S. Pat. No. 6,466,638 discloses a method for the calibration.

A plurality of beads are embedded in the phantom ph, and the structure is taught in, for example, U.S. Pat. No. 5,442,674. The substantially spherical beads embedded in the phantom ph are arranged in the substrate. Positions of the beads in the substrate are known, and the X-ray contrast between the beads and the substrate is enough large to resolve the beads in the X-ray projection. The beads have identification information such that they are specified on the X-ray projection.

The beads of the phantom ph are formed of, for example, tungsten carbide and arranged in a spiral manner. The center of each of the beads determines the accuracy of the subpixel. The maximum pellet is specified on the projection and used to align the other pellets. The pellets aligned on the projection are adjusted to known three-dimensional pellet positions.

When the phantom ph is projected on the detection surface of the X-ray detector 13, xyz coordinates of a voxel positioned in the center of each of the spherical beads are known, and a pixel positioned in the projection center of each of beads is defined by the column position c and the row position l.

The relation of the position (x, y, z) of the specific point on the phantom ph and the position (c, l) on the detection surface serving as a 2D projection image plane is generally provided by the following conversion expression (1).

$$\lambda [cl1]^T = M[xyz1]^T \quad (1)$$

The superscript "T" represents replacement of the position vectors (cl1) and (xyz1), and M represents a correction matrix including matrix elements $m_{11}$, $m_{12}$, $m_{13}$, $m_{14}$, $m_{21}$, $m_{22}$, $m_{23}$, $m_{24}$, $m_{31}$, $m_{32}$, $m_{33}$, and $m_{34}$ serving as the correction coefficients. In addition, $\lambda$ represents a scale coefficient to align the coordinate system.

To supplement, the correction matrix M is calibration data (wobble table), and the correction matrix can be developed into the format in the following expression (2) (the scale coefficient $\lambda$ depends on the correction matrix M).

$$\lambda \begin{Bmatrix} c \\ l \\ 1 \end{Bmatrix} = \begin{bmatrix} m_{11} & m_{12} & m_{13} & m_{14} \\ m_{21} & m_{22} & m_{23} & m_{24} \\ m_{31} & m_{32} & m_{33} & m_{34} \end{bmatrix} \begin{Bmatrix} x \\ y \\ z \\ 1 \end{Bmatrix} \quad (2)$$

The calibration function 443 calculates such calibration data, and stores the calibration data in the memory 41. The calibration data may be data associating the projection position of the bead on the detection surface of the X-ray detector 13 with the position of the bead on a three-dimensional space of the phantom ph.

The calculating function 444 acquires, from the memory 41, projection data acquired by executing rotation imaging for the phantom ph with the X-ray generator 12 and the X-ray detector 13 that are arranged rotatably around the phantom ph. The calculating function 444 also calculates three-dimensional position information of each of the X-ray generator 12 and the X-ray detector 13 during rotation imaging, on the basis of the projection data.

In this operation, the calculating function 444 may calculate each of pieces of three-dimensional position information on the basis of the calibration data stored in the memory 41. For example, the calculating function 444 can calculate the three-dimensional position PXp (x, y, z) of the focal point Xp of the X-ray tube 121 and the three-dimensional position PDp (x, y, z) of any specific point on the detector surface using arithmetic operations of geometry and algebra on the basis of the expression (2), as represented by the following expression (3) and expression (4).

$$PXp(x,y,z) = PXp(M) \quad (3)$$

$$PDp(x,y,z) = PDp(M) \quad (4)$$

The relation between the expression (2) and the expression (3) will be described hereinafter.

When an equation of a straight line is established by substituting two points "P1=(c, l)=(c1, l1)" and "P2=(c, l)=(c2, l2)" in the expression (2), the solution (x, y, z) of the equation of the straight line is the coordinates PXp (x, y, z) of the focal point Xp of the X-ray tube 121.

The relation between the expression (2) and the expression (4) will be described hereinafter.

The spatial position of the detector surface can be displayed with three any specific points. Suppose that the origin is (c=0, l=0), and the detector surface formed of the c axis and the l axis will be described as an example.

When three points "P0=(c, l)=(0, 0)", "P1=(c, l)=(1, 0)", and "P2=(c, l)=(0, 1)" are substituted in the expression (2) and the relation of the unit "P0P1×P0P2 (x, y, z)=M (m31, m32, m33) is used, a scale coefficient λ is determined. Using the determined scale coefficient provides a coordinate system formed of the origin P0 (x, y, z), the unit vector P0P1 (x, y, z) of the c axis, the unit vector P0P2 (x, y, z) of the l axis, and the normal unit vector P0P1×P0P2 (x, y, z) of the detector surface, with respect to the detector surface. This structure enables calculation of the spatial position PDp (x, y, z) of the detector surface corresponding to any point (c, l).

To supplement, the X-ray diagnostic apparatus 1 use a phantom to calibrate the correlation (wobble table) between the projection plane and the reconstruction space, and calculates the spatial position (three-dimensional position) in calibration imaging of the X-ray tube focal point and the X-ray detector surface on the basis of the wobble table. The "calibration imaging" may also be referred to as "projection imaging" or "3D imaging scan". The term "rotation imaging" described above includes the terms "calibration imaging", "projection imaging", and "3D imaging scan".

In addition, the calculating function 444 may calculate first motion state data of the X-ray generator on the basis of the three-dimensional position information of the X-ray generator 12, and calculate second motion state data of the X-ray detector on the basis of the three-dimensional position information of the X-ray detector 13. For example, the calculating function 444 may calculate first motion image data indicating a deviation of the three-dimensional position information of the X-ray generator 12 from the standard locus position of the X-ray generator 12. As another example, the calculating unit 444 may calculate second motion state data indicating a deviation of the three-dimensional position information of the X-ray detector 13 from the standard locus position of the X-ray detector 13. Herein, the first motion state data may be time-series data indicating oscillation of the X-ray generator 12 caused by rattling or elastic deformation of the X-ray diagnostic apparatus during rotation imaging along time series. The second motion state data may be time-series data indicating oscillation of the X-ray detector 13 caused by rattling or elastic deformation of the X-ray diagnostic apparatus during rotation imaging along time series.

In addition, the calculating function 444 may calculate a first index on the basis of the first motion state data, and calculate a second index on the basis of the second motion state data. Elements that can be used as the first index and the second index are a magnitude of the difference vector and a frequency shift quantity described later. However, the structure is not limited thereto but, for example, statistical information, such as a mean value and a maximum value, may be properly used as the first index and the second index. The term "index" may be replaced by the term "characteristic value".

The determination function 445 determines whether the first index has exceeded a first threshold, and outputs "abnormality" if the first index has exceeded the first threshold. The determination function 445 also determines whether the second index has exceeded a second threshold, and outputs "abnormality" if the second index has exceeded the second threshold. If "abnormality" is output, the determination function 445 may transmit a maintenance request for the abnormality to a management terminal (not illustrated).

The prediction function 446 predicts the time period in which an abnormality will occur in the X-ray diagnostic apparatus 1 on the basis of at least one of the first index and the second index. For example, the prediction function 446 may predict the time period in which an abnormality will occur, on the basis of the magnitude of at least one of the first index and the second index. The prediction function 446 may also predict the time period in which an abnormality will occur, on the basis of change with time of at least one of the first index and the second index. If the prediction function 446 predicts the time period in which an abnormality will occur, the prediction function 446 may also transmit a maintenance request based on the prediction result to the management terminal (not illustrated). Specifically, the maintenance request may include a determination result indicating "abnormality" and a result of prediction of the time period in which an abnormality will occur. The abnormality determination result may include estimation of the abnormal part. The prediction of the time period in which an abnormality will occur may include data indicating the abnormality tendency (change with time). The term "maintenance request" may be substituted by another word, such as "apparatus inspection result" and "report". In a case of "report" or the like, the report may be transmitted to the management terminal even when the determination result does not always indicate "abnormality". In this case, for example, a report including a determination result indicating "normal" and a result of prediction of the time period in which an abnormality will occur may be transmitted to the management terminal.

The network interface 45 is a circuit to connect the console apparatus 40 to a network Nw and communicate with another device. For example, a network interface card (NIC) can be used as the network interface 45. The following explanation omits description to the effect that the network interface 45 is interposed therebetween in communication with another device.

The memory 41, the calculating function 444, the determination function 445, and the prediction function 446 of the processing circuitry 44, and the network interface 45 form the medical image processing apparatus 46. The determination function 445, the prediction function 446, and the network interface 45 are optional and additional elements and may be omitted.

Figure 3:
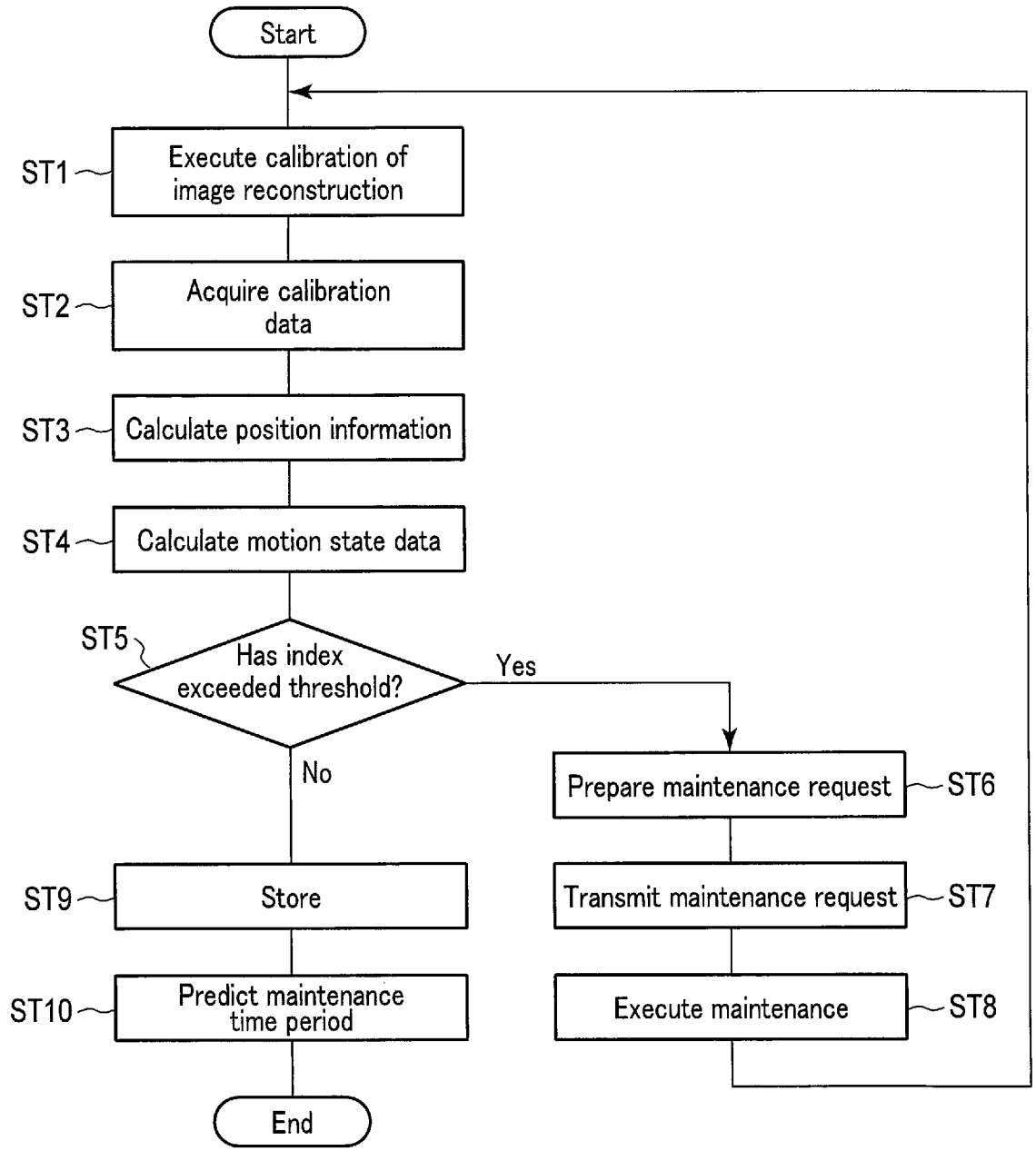
FIG. 3 is a flowchart for explaining operations according to the first embodiment.
Figure 4:
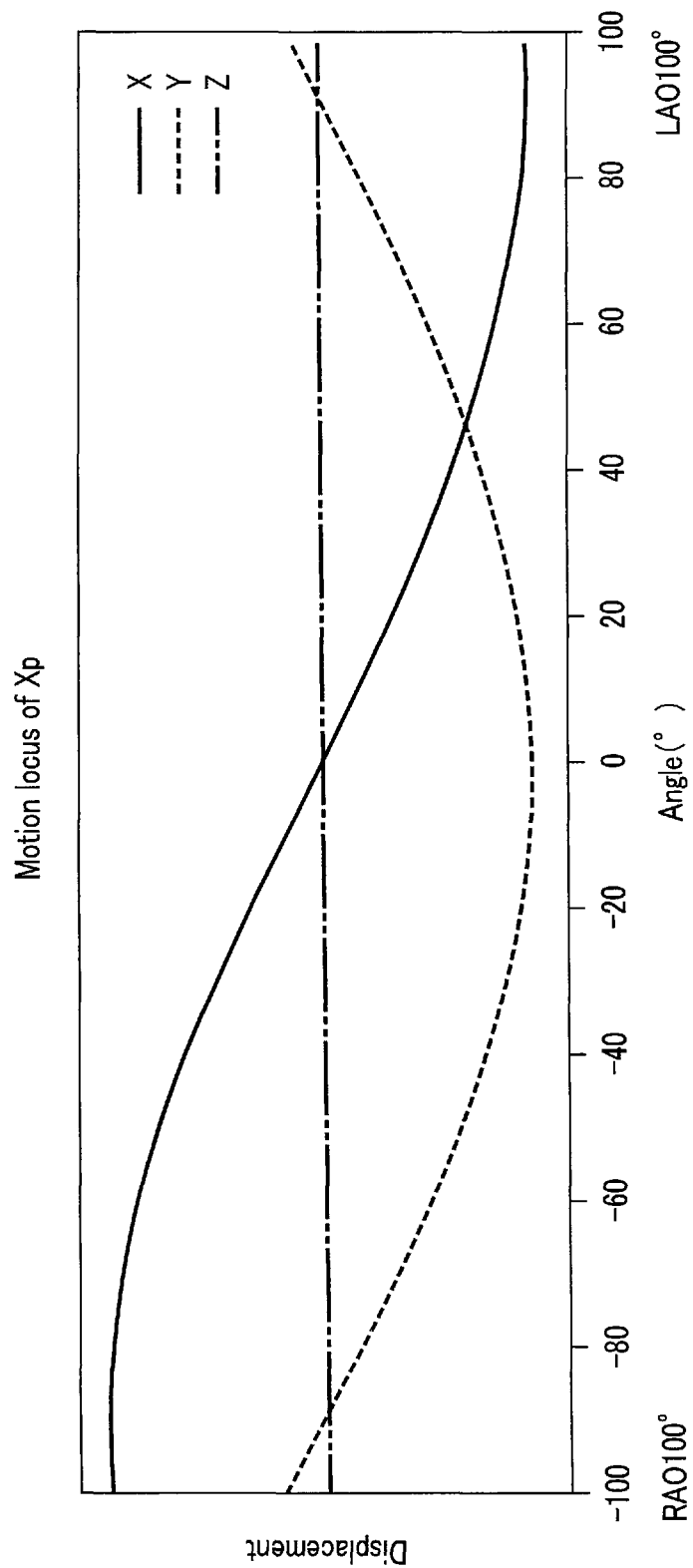
FIG. 4 is a schematic diagram for explaining a motion locus of an X-ray focal point according to the first embodiment.
Figure 5:
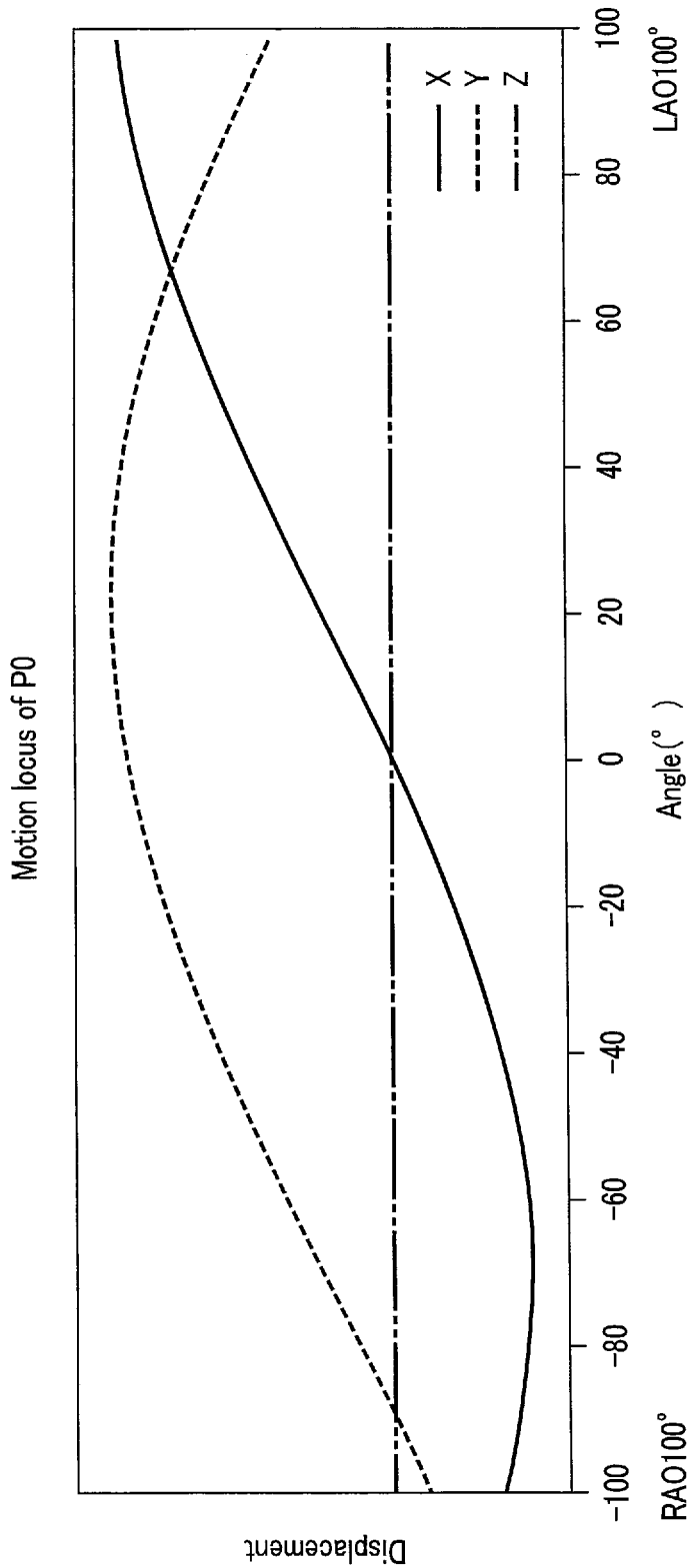
FIG. 5 is a schematic diagram for explaining a motion locus of the origin of an X-ray detector according to the first embodiment.

The following is an explanation of operations of the X-ray diagnostic apparatus and the medical image processing apparatus configured as described above, with reference to the flowchart of FIG. 3 and the schematic diagrams of FIG. 4 and FIG. 5.

First, at Step ST1, the processing circuitry 44 of the X-ray diagnostic apparatus 1 controls the imaging apparatus 10 in response to an operation of the input interface 43 by the operator, and starts rotation imaging for the phantom ph. In this manner, while rotating around the phantom ph, the X-ray generator 12 generates X-rays, and the X-ray detector 13 detects the X-rays transmitted through the phantom ph and successively generates projection data. The successively generated projection data is stored from the X-ray detector 13 in the memory 41. The processing circuitry 44 calculates calibration data (M) associating the projection position (c, l) of the bead on the detection surface of the X-ray detector 13 with the position (x, y, z) of the bead on the three-dimensional space of the phantom ph, on the basis of the projection data in the memory 41, as indicated with the expression (1)

and the expression (2) described above. Thereafter, the processing circuitry 44 stores the calibration data in the memory 41. In this manner, calibration is executed (Step ST1).

After Step ST1, the processing circuitry 44 acquires, at Step ST2, projection data acquired by executing rotation imaging for the phantom ph from the memory 41. The processing circuitry 44 also acquires calibration data from the memory 41 (Step ST2).

After Step ST2, the processing circuitry 44 calculates, at Step S3, three-dimensional position information of each of the X-ray generator 12 and the X-ray detector 13 during rotation imaging by the expression (3) and the expression (4) described above, on the basis of the projection data and the calibration data acquired from the memory 41 (Step ST3).

Each piece of three-dimensional information (x, y, z) may be expressed as a motion locus, as illustrated in FIG. 4 and FIG. 5, with the horizontal axis indicating the rotation angle of the C-arm 14 and the vertical axis indicating displacement. FIG. 4 is a schematic diagram illustrating a motion locus of an X-ray focal point Xp of the X-ray tube 121 in rotation imaging calculated with the expression (3). FIG. 5 is a schematic diagram illustrating a motion locus of the origin P0 of the X-ray detector 13 in rotation imaging calculated with the expression (4). In FIG. 4 and FIG. 5, the term "RAO" is an abbreviation of "Right Anterior Oblique View" (first oblique position). The term "LAO" is an abbreviation of "Left Anterior Oblique View" (second oblique position). Specifically, FIG. 4 and FIG. 5 illustrate a motion locus of each of the focal point Xp of the X-ray tube 121 and the origin PO of the X-ray detector 13 in the case where the C-arm 14 is rotated around the z axis within an angle range from RAO 100° to the LAO 100° via 0°.

After Step ST3, at Step ST4, the processing circuitry 44 calculates first motion state data of the X-ray generator 12 on the basis of the three-dimensional position information of the X-ray generator 12. The processing circuitry 44 also calculates second motion state data of the X-ray detector 13 on the basis of the three-dimensional position information of the X-ray detector 13. For example, the processing circuitry 44 may calculate first motion state data indicating a deviation of the three-dimensional position information of the X-ray generator 12 from the standard locus position of the X-ray generator 12. In addition, for example, the processing circuitry 44 may calculate second motion state data indicating a deviation of the three-dimensional position information of the X-ray detector 13 from the standard locus position of the X-ray detector 13. Thereafter, the processing circuitry 44 calculates a first index on the basis of the first motion state data. The processing circuitry 44 also calculates a second index on the basis of the second motion state data. Elements that can be used as the first index and the second index are indexes, such as a magnitude of the difference vector and a frequency shift quantity described later. However, the structure is not limited thereto but, for example, statistical information, such as a mean value, a mode, and a maximum value, may be properly used as the first index and the second index. In this example, suppose that the maximum value of the first motion state data indicating a deviation is used as the first index, and the maximum value of the second motion state data indicating a deviation is used as the second index.

After Step ST4, at Step ST5, the processing circuitry 44 determines whether the first index has exceeded the first threshold. The processing circuitry 44 also determines whether the second index has exceeded the second threshold.

As a result of Step ST5, in the case where the index has exceeded the first threshold or the second threshold, the processing circuitry 44 outputs "abnormality". In this operation, the processing circuitry 44 prepares a maintenance request for the abnormality (Step ST6), and transmits the maintenance request to the management terminal (not illustrated) (Step ST7). Herein, the maintenance request may be any request as long as it includes the index and the threshold used for the determination at Step ST5. The management terminal displays the received maintenance request to prompt the worker to execute maintenance for the X-ray diagnostic apparatus 1 serving as the transmission source of the maintenance request. After Step ST7, at Step ST8, the worker executes maintenance for the X-ray diagnostic apparatus 1. After Step ST8, the operation of the X-ray diagnostic apparatus 1 proceeds to Step ST1.

By contrast, as a result of Step ST5, in the case where the threshold has not exceeded the first threshold or the second threshold, the processing circuitry 44 stores the first index and the second index in the memory 41 (Step ST9). The processing circuitry 44 may store the first motion state data and the second motion state data in the memory 41 instead of, or in addition to, the first index and the second index.

After Step ST9, at Step ST10, the processing circuitry 44 predicts the time period in which an abnormality will occur in the X-ray diagnostic apparatus 1, on the basis of at least one of the first index and the second index. For example, the processing circuitry 44 may predict the time period in which an abnormality will occur, on the basis of the magnitude of at least one of the first index and the second index. As another example, the prediction function 466 may predict the time period in which an abnormality will occur, on the basis of change with time of at least one of the first index and the second index. In either case, after the prediction, the processing circuitry 44 predicts a maintenance time period such that the maintenance time period is set earlier than the time period in which an abnormality will occur, and transmits a maintenance request including a prediction result of one of the time period in which an abnormality will occur and the maintenance time period to the management terminal (not illustrated).

After Step ST10, the processing circuitry 44 finishes the processing.

As described above, according to the first embodiment, the apparatus calculates the three-dimensional position information of each of the X-ray generator and the X-ray detector during rotation imaging, on the basis of projection data acquired by executing the rotation imaging for the phantom with the X-ray generator and the X-ray detector arranged rotatably around the phantom. Each of the calculated three-dimensional position information reflects the mechanical state of the X-ray diagnostic apparatus. This structure enables diagnosis of the mechanical state of the X-ray diagnostic apparatus, on the basis of the three-dimensional position information, before an artifact occurs in the reconstructed image.

To supplement, the apparatus requires no mechanisms (such as external sensors) or works to be specially added to conventional X-ray diagnostic apparatuses, and enables more accurate evaluation and determination of the state of the X-ray diagnostic apparatus by evaluating the pieces of three-dimensional position information indicating the spatial positions of the X-ray generator and the X-ray detector. In addition, the structure enables recognition of the mechanical state and/or the cause of malfunction of the X-ray diagnostic apparatus by analyzing the three-dimensional position information.

In addition, according to the first embodiment, a plurality of beads may be embedded in the phantom. Each of the three-dimensional position information may be calculated on the basis of calibration data associating the projection position of the bead on the detection surface of the X-ray detector with the position of the bead on the three-dimensional space of the phantom. In this case, the structure enables calculation of the three-dimensional position information on the basis of calibration data acquired by execution of calibration, in addition to the advantageous effects described above.

To supplement, the apparatus requires no mechanisms (such as external sensors) or works to be specially added to conventional X-ray diagnostic apparatuses, and enables recognition of three-dimensional position information of each of the X-ray generator and the X-ray detector by utilizing results of calibration necessary for image reconstruction.

In addition, according to the first embodiment, the structure may calculate first motion state data indicating a deviation of the three-dimensional position information of the X-ray generator from the standard locus position of the X-ray generator. In addition, the structure may calculate second motion state data indicating a deviation of the three-dimensional position information of the X-ray detector from the standard locus position of the X-ray detector. In this case, the first motion state data and the second motion state data more clearly reflect the mechanical state of the X-ray diagnostic apparatus, in comparison with each of the three-dimensional position information. This structure enables easier diagnosis of the mechanical state of the X-ray diagnostic apparatus, on the basis of the first motion state data and the second motion state data, before an artifact occurs in the reconstructed image.

In addition, according to the first embodiment, the structure may calculate the first index on the basis of the first motion state data, and calculate the second index on the basis of the second motion state data. In this case, the first index and the second index can be expected to more clearly reflect the mechanical state of the X-ray diagnostic apparatus, in comparison with each of the motion state data. This structure can be expected to achieve easier diagnosis of the mechanical state of the X-ray diagnostic apparatus, on the basis of the first index and the second index.

In addition, according to the first embodiment, the structure may determine whether the first index has exceeded the first threshold, and may output "abnormality" if the first index has exceeded the first threshold. In addition, the structure may determine whether the second index has exceeded the second threshold, and may output "abnormality" if the second index has exceeded the second threshold. In this case, the structure enables determination based on the criteria according to the first threshold and the second threshold, and output "abnormality", in addition to the advantageous effects described above. For example, in the case of executing determination with strict criteria, the first threshold and the second threshold to be used are smaller than those in the case of using moderate criteria. In the case of executing determination with moderate criteria, the first threshold and the second threshold to be used are larger than those in the case of using strict criteria.

In addition, according to the first embodiment, the structure may predict the time period in which an abnormality will occur in the X-ray diagnostic apparatus on the basis of at least one of the first index and the second index. For example, as the value of the index increases, the difference from the threshold decreases and the time period in which an abnormality will occur is closer at hand. Accordingly, it is possible to predict the time period in which an abnormality will occur, on the basis of at least the magnitude of at least one of the first index and the second index. In this case, the structure enables execution of maintenance earlier than the time period of occurrence of an abnormality, in addition to the advantageous effects described above.

With respect to the effects, a supplementary explanation will be made using a comparative example of detecting a difference (artifact) from the actual shape of the imaged phantom with a CT reconstructed image with the X-ray diagnostic apparatus. In the comparative example, the phantom is subjected to rotation imaging to reconstruct a projection image, the characteristic value of the artifact of the reconstructed image is calculated, and the characteristic value is associated with a malfunction database prepared in advance to diagnose the mechanical state of the X-ray diagnostic apparatus. The comparative example like this cannot recognize the abnormality tendency of the apparatus, because malfunction can be detected only after an artifact occurs. By contrast, the first embodiment enables prediction of the time period in which an abnormality will occur, as described above.

In addition, according to the first embodiment, the apparatus may predict the time period in which an abnormality will occur in the X-ray diagnostic apparatus, on the basis of change with time of at least one of the first index and the second index. For example, by determining future change of the index by extrapolation on the basis of change with time of the index, it is possible to predict the time period in which the index will exceed the threshold as the time period in which an abnormality will occur. This structure enables execution of maintenance earlier than the time period in which an abnormality will occur, in addition to the advantageous effects described above. In addition, because the time period is predicted on the basis of change with time of the index, improvement in prediction accuracy can be expected in comparison with the case of predicting the time period on the basis of the magnitude of the index.

Second Embodiment

Figure 6:
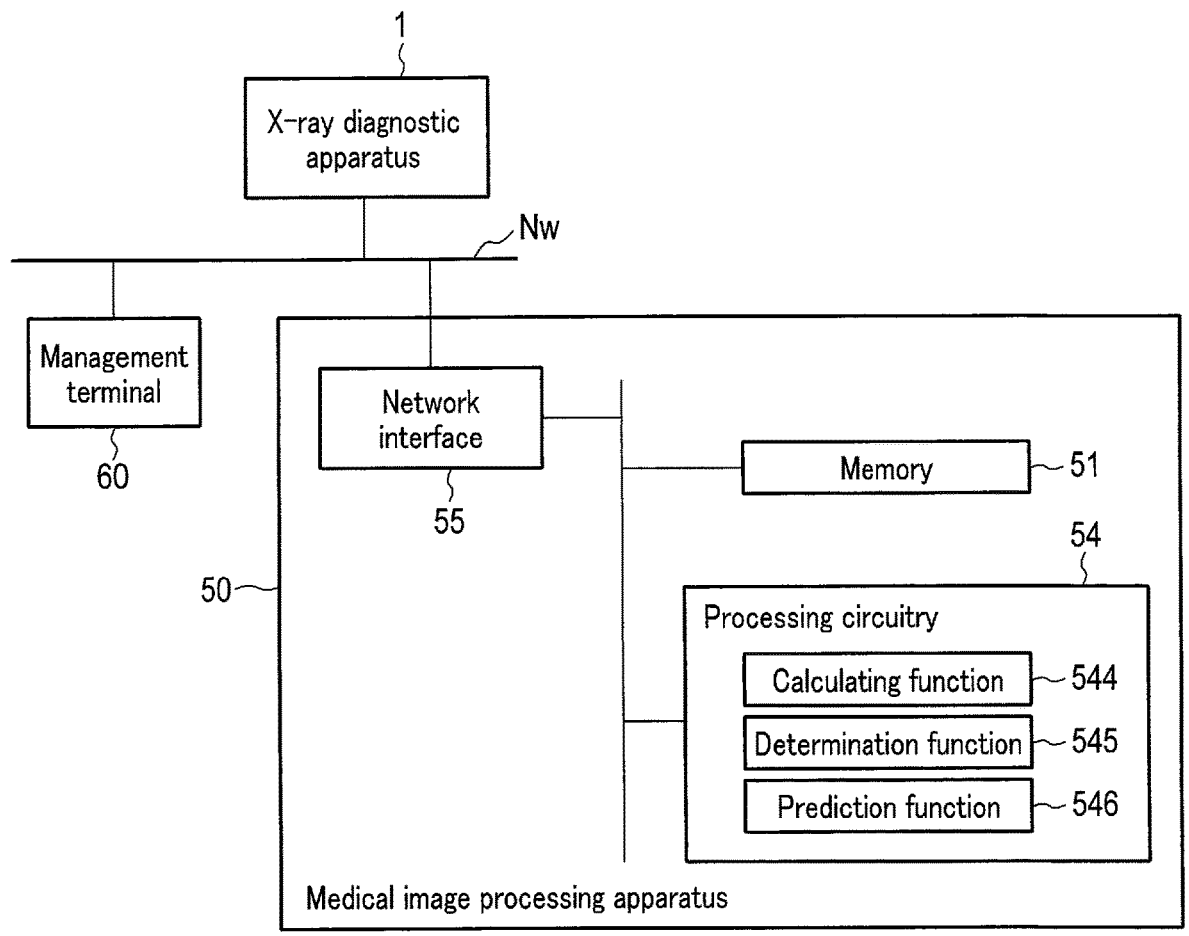
FIG. 6 is a block diagram showing a medical image processing apparatus and a peripheral structure thereof according to a second embodiment.

The following is an explanation of a medical image processing apparatus according to a second embodiment with reference to FIG. 6. In the following explanation, constituent elements substantially the same as those in the drawings described above are denoted by the same reference numerals, and a detailed explanation thereof will be omitted. Different constituent elements will be mainly explained hereinafter.

The second embodiment has a structure including a medical image processing apparatus 50 separated from an X-ray diagnostic apparatus 1, instead of the medical image processing apparatus 46 included in the X-ray diagnostic apparatus 1.

Herein, the medical image processing apparatus 50 is a management server capable of communicating with the X-ray diagnostic apparatus 1 and a management terminal 60 via a network Nw. The medical image processing apparatus 50 includes a memory 51, processing circuitry 54, and a network interface 55.

The memory 51 has the same structure as the memory 41 described above. For example, the memory 51 includes a memory main member recording electrical information, such as a ROM, a RAM, a HDD, and an image memory, and a peripheral circuit, such as a memory controller and a memory interface, accompanying the memory main member. The memory 51 stores, for example, a program executed with the processing circuitry 54, data received from the X-ray diagnostic apparatus 1, data used for processing with the processing circuitry 54, data being processed, and processed data. The data includes calibration data and/or projection data described later. In the same manner as described above, the projection data is data acquired by execution rotation imaging for a phantom ph with an X-ray generator 12 and an X-ray detector 13 arranged rotatably around the phantom ph, and transmitted from the X-ray diagnostic apparatus 1 to the medical image processing apparatus 50. The memory 51 is another example of the storage unit.

The processing circuitry 54 is a processor calling and executing a program in the memory 51 to achieve a calculating function 544, a determination function 545, and a prediction function 546 corresponding to the program. Examples of the program of this type include a mechanical state detection program to cause the computer (medical image processing apparatus 46) to achieve the calculating function 544. The mechanical state detection program may cause the computer to further achieve the determination function 545, the prediction function 546, and the image processing function 442, if necessary. Distribution of the functions, such as the calculating function 544, the determination function 545, and the prediction function 546, is an example and is not specifically limited. For example, the calculating function 544 may bear part of the determination function 545 or the prediction function 546. In the same manner, the determination function 545 may bear part of the calculating function 544 or the prediction function 546. Also in the same manner, the prediction function 546 may bear part of the calculating function 544 or the determination function 545. In addition, FIG. 6 illustrates that the single processing circuitry 54 achieves the calculating function 544, the determination function 545, and the prediction function 546, but a plurality of independent processors may be combined to form the processing circuit, and the functions may be achieved by executing the program with the processors. The calculating function 544, the determination function 545, and the prediction function 546 may be referred to as "calculating circuit", "determination circuit", and "prediction circuit", respectively, and may be mounted as individual hardware circuits. The processing circuitry 54 is an example of a first calculating unit, a second calculating unit, a third calculating unit, a fourth calculating unit, a first determination unit, a second determination unit, a third determination unit, and a prediction unit.

The calculating function 544 has the same structure as that of the calculating function 444 described above. For example, the calculating function 544 acquires, from the memory 51, projection data acquired by executing rotation imaging for the phantom ph with the X-ray generator 12 and the X-ray detector 13 that are arranged rotatably around the phantom ph. The calculating function 544 also calculates three-dimensional position information of each of the X-ray generator 12 and the X-ray detector 13 during rotation imaging, on the basis of the projection data.

The determination function 545 has the same structure as that of the determination function 445 described above.

The prediction function 546 has the same structure as that of the prediction function 446 described above.

The management terminal 60 is a terminal device capable of communicating with the X-ray diagnostic apparatus 1 and the medical image processing apparatus 50 via the network Nw. For example, a personal computer (PC) or a workstation can be properly used as the management terminal 60.

The other constituent elements are the same as those of the first embodiment. However, in the medical image processing apparatus 46 in the X-ray diagnostic apparatus 1, the calculating function 444, the determination function 445, and the prediction function 446 described above are omitted because the medical image processing apparatus 50 includes the calculating function 544, the determination function 545, and the prediction function 546 that are similar to them.

Figure 7:
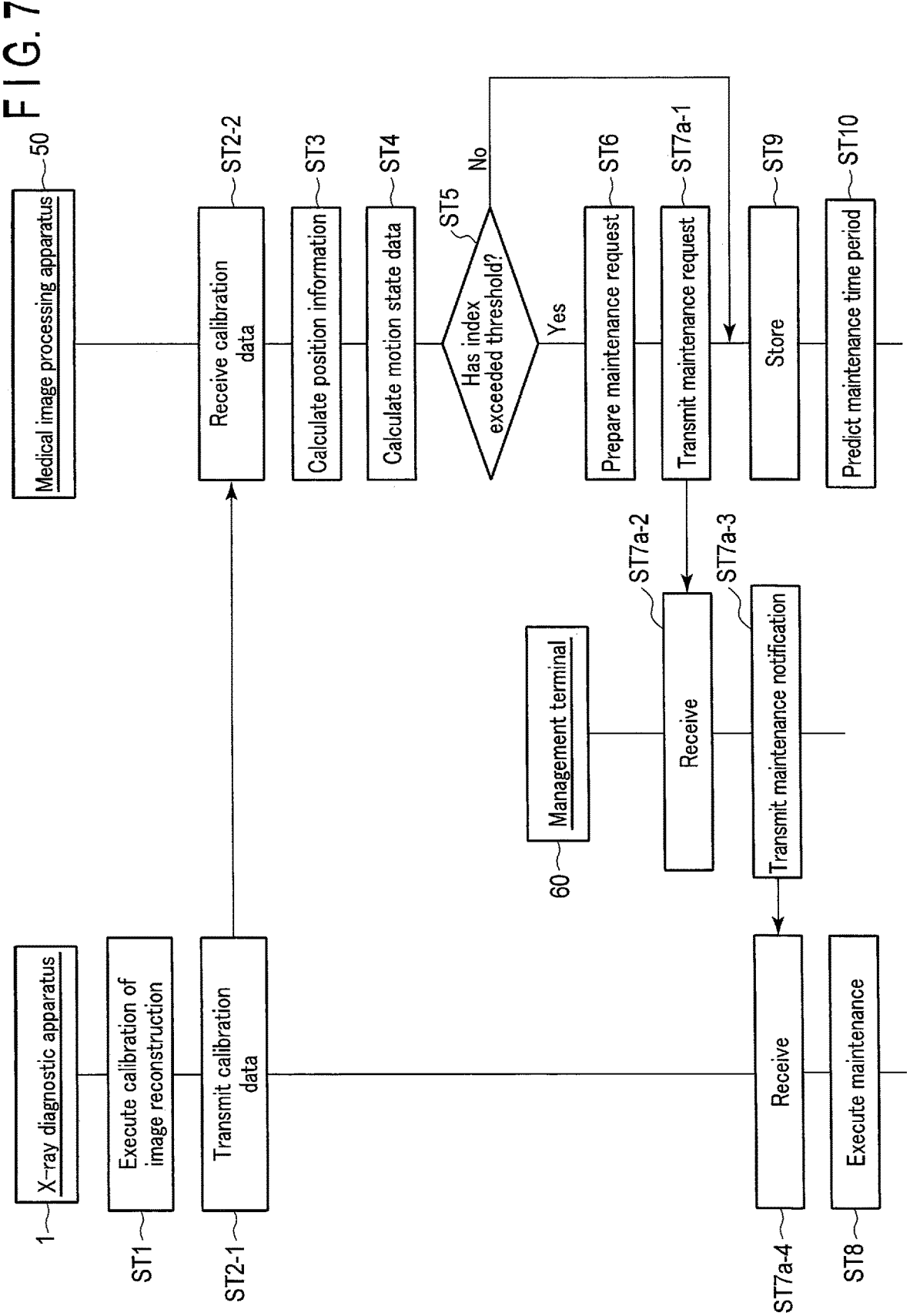
FIG. 7 is a flowchart for explaining operations according to the second embodiment.

The following is an explanation of operations of the X-ray diagnostic apparatus and the medical image processing apparatus configured as described above, with reference to the flowchart of FIG. 7.

Now, Step ST1 is executed in the same manner as described above. Specifically, the X-ray diagnostic apparatus 1 executes rotation imaging for the phantom ph, and stores the acquired projection data in the memory 41. In addition, the processing circuitry 44 of the X-ray diagnostic apparatus 1 calculates calibration data (M) on the basis of the projection data in the memory 41, and stores the calibration data (M) in the memory 41. In this manner, calibration is executed (Step ST1).

After Step ST1, at Step ST2-1, the processing circuitry 44 of the X-ray diagnostic apparatus 1 acquires calibration data from the memory 41, and transmits the calibration data to the medical image processing apparatus 50. Around the time of the transmission, the processing circuitry 44 of the X-ray diagnostic apparatus 1 acquires projection data from the memory 41, and transmits the projection data to the medical image processing apparatus 50.

After Step ST2-1, at Step ST2-2, the medical image processing apparatus 50 receives the calibration data, and stores the calibration data in the memory 51. Around the time of the reception, the medical image processing apparatus 50 receives the projection data, and stores the projection data in the memory 51.

After Step ST2-2, Step ST3 is executed in the same manner as described above, in which the processing circuitry 54 calculates three-dimensional position information of each of the X-ray generator 12 and the X-ray detector 13 during rotation imaging by the expression (3) and the expression (4) described above, on the basis of the projection data and the calibration data acquired from the memory 51 (Step ST3).

After Step ST3, Step ST4 is executed in the same manner as described above, in which the processing circuitry 54 calculates first motion state data of the X-ray generator 12 on the basis of the three-dimensional position information of the X-ray generator 12. In the same manner, the processing circuitry 54 also calculates second motion state data of the X-ray detector 13 on the basis of the three-dimensional position information of the X-ray detector 13. In the same manner, the processing circuitry 44 also calculates a first index on the basis of the first motion state data, and calculates a second index on the basis of the second motion state data.

After Step ST4, Step ST4 is executed in the same manner as described above, in which the processing circuitry 54 determines whether the first index has exceeded the first threshold. The processing circuitry 54 also determines whether the second index has exceeded the second threshold.

As a result of Step ST5, in the case where the index has exceeded the first threshold or the second threshold, the processing circuitry 54 outputs "abnormality". In this operation, the processing circuitry 54 prepares a maintenance request for the abnormality (Step ST6), and transmits the maintenance request to the management terminal 60 (Step ST7a-1). Herein, the maintenance request may be any request as long as it includes the index and the threshold used for the determination at Step ST5. The management terminal receives the maintenance request (Step ST7a-2), and displays the received maintenance request to prompt the worker to execute maintenance for the X-ray diagnostic apparatus 1 serving as the transmission source of the maintenance request. In addition, by an operation by the operator, the management terminal 60 prepares a maintenance notification including information (such as the date and the contact address) on execution of the maintenance, and transmits the maintenance notification to the X-ray diagnostic apparatus 1 (Step ST7a-3). The X-ray diagnostic apparatus 1 receives the maintenance notification (Step ST7a-4), and displays the maintenance notification to notify the operator of the X-ray diagnostic apparatus 1 of the information on execution of the maintenance in the maintenance notification.

After Step ST7a-4, at Step ST8 similar to the step described above, the worker executes maintenance for the X-ray diagnostic apparatus 1. After Step ST8, the operation of the X-ray diagnostic apparatus 1 proceeds to Step ST1.

By contrast, as a result of Step ST5, in the case where the threshold has not exceeded the first threshold or the second threshold, the processing circuitry 54 stores the first index and the second index in the memory 51 (Step ST9). The processing circuitry 54 may store the first motion state data and the second motion state data in the memory 51 instead of, or in addition to, the first index and the second index.

After Step ST9, Step ST10 is executed in the same manner as described above, in which the processing circuitry 54 predicts the time period in which an abnormality will occur in the X-ray diagnostic apparatus 1, on the basis of at least one of the first index and the second index. The processing circuitry 54 may predict the time period in which an abnormality will occur, on the basis of change with time of at least one of the first index and the second index. In either case, after the prediction, the processing circuitry 44 predicts a maintenance time period such that the maintenance time period is set earlier than the time period in which an abnormality will occur, and transmits a maintenance request including a prediction result of one of the time period in which an abnormality will occur and the maintenance time period to the management terminal 60.

After Step ST10, the processing circuitry 54 finishes the processing.

As described above, according to the second embodiment, advantageous effects similar to those of the first embodiment can be acquired even with the structure including the medical image processing apparatus 50 separated from the X-ray diagnostic apparatus 1. This is the same also in each of the following embodiments. Specifically, each of the following embodiments is explained as a specific example or a modification of the first embodiment, but the structure is not limited thereto. Each of the following embodiments may be a specific example or a modification of the second embodiment.

Third Embodiment

The following is an explanation of an X-ray diagnostic apparatus according to the third embodiment.

The third embodiment is a specific example of the first embodiment, and has a structure in which each of the first notion state data and the second motion state data is time-series data, and each of the first index and the second index is a magnitude of the difference vector.

Herein, the first motion state data is time-series data indicating oscillation of (the focal point Xp of the X-ray tube 121 in) the X-ray generator 12 caused by rattling or elastic deformation of the X-ray diagnostic apparatus 1 during rotation imaging along time series. The first index is a magnitude of a first difference vector between position vectors of the X-ray generator 12 calculated from the first motion state data for every certain time.

The second motion state data is time-series data indicating oscillation of (the origin P0 of) the X-ray detector 13 caused by rattling or elastic deformation of the X-ray diagnostic apparatus 1 during rotation imaging along time series. The second index is a magnitude of a second difference vector between position vectors of the X-ray detector 13 calculated from the second motion state data for every certain time.

With this structure, the calculating function 444 of the processing circuitry 44 may calculate a first tangent motion vector of the X-ray generator 12 on the basis of the first difference vector, in the case where "abnormality" is output due to the magnitude of the first difference vector exceeding the first threshold, in addition to the function described above. In the same manner, the calculating function 444 may calculate a second tangent motion vector of the X-ray detector 13 on the basis of the second difference vector, in the case where "abnormality" is output due to the magnitude of the second difference vector exceeding the second threshold.

The determination function 445 may determine degree of freedom of motion most parallel with the first tangent motion vector and the second tangent motion vector, on the basis of the first tangent motion vector and the second tangent motion vector and the degree of freedom of motion of each of a plurality of coupling portions in the X-ray diagnostic apparatus 1. The determination function 445 may also output "abnormality" of the coupling portion having the determined degree of freedom of motion.

The other constituent elements are the same as those of the first embodiment.

With the structure described above, at Step ST4 described above, the processing circuitry 44 calculates first motion state data indicating a deviation of the three-dimensional position information of the X-ray generator 12 from the standard locus position of the X-ray generator 12. The first motion state data is time-series data indicating oscillation of (the focal point Xp of the X-ray tube 121 in) the X-ray generator 12 caused by rattling or elastic deformation of the X-ray diagnostic apparatus 1 during rotation imaging along time series.

In addition, the processing circuitry 44 calculates second motion state data indicating a deviation of the three-dimensional position information of the X-ray detector 13 from the standard locus position of the X-ray detector 13. The second motion state data is time-series data indicating oscillation of (the origin P0 of) the X-ray detector 13 caused by rattling or elastic deformation of the X-ray diagnostic apparatus 1 during rotation imaging along time series.

Figure 8:
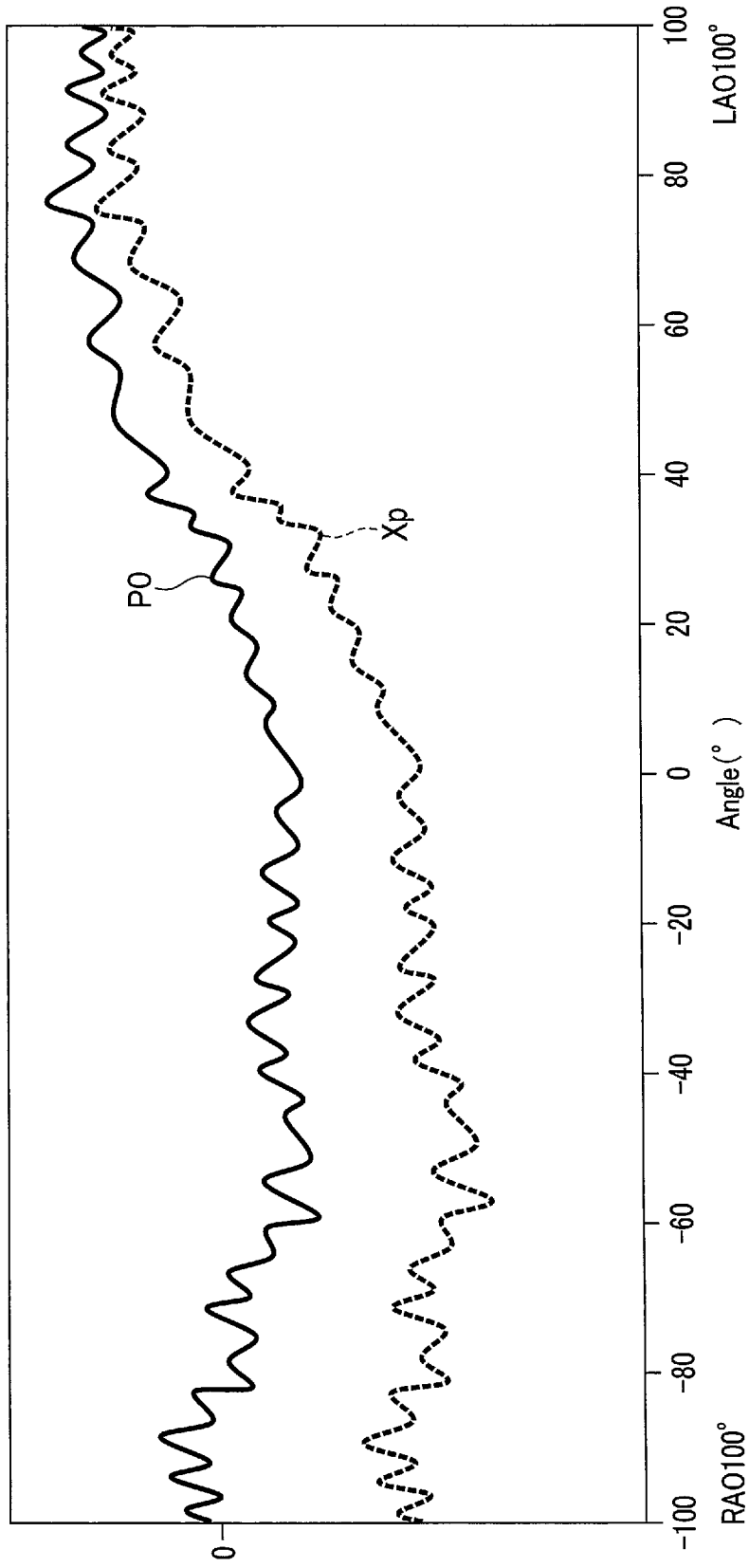
FIG. 8 is a schematic diagram for explaining motion state data acquired from FIG. 4 and FIG. 5.

To supplement, each of the pieces of three-dimensional spatial information illustrated in FIG. 4 and FIG. 5 described above includes movement information (standard locus position) of the rigid body in the driven state and information (oscillation information) of backlash of the coupling portion and/or elastic deformation of each of parts. For this reason, by analyzing time-series data of the spatial positions of the focal point Xp and the detector origin P0, the data can be resolved into the standard locus position and each of mode of the oscillation information. FIG. 8 is a schematic diagram for explaining motion state data acquired from FIG. 4 and FIG. 5, and illustrates time-series data (first motion state data and second motion state data) of oscillation information calculated from the three-dimensional spatial information. In FIG. 8, each pieces of the motion state data is illustrated with the horizontal axis indicating the rotation angle of the C-arm 14 and the vertical axis indicating displacement.

The processing circuitry 44 also calculates a magnitude of the first difference vector between position vectors of the X-ray generator 12 calculated from the first motion state data for every certain time. The magnitude of the first difference vector is an example of the first index. The processing circuitry 44 also calculates a magnitude of the second difference vector between position vectors of the X-ray detector 13 calculated from the second motion state data for every certain time. The second difference vector is an example of the second index.

Figure 9:
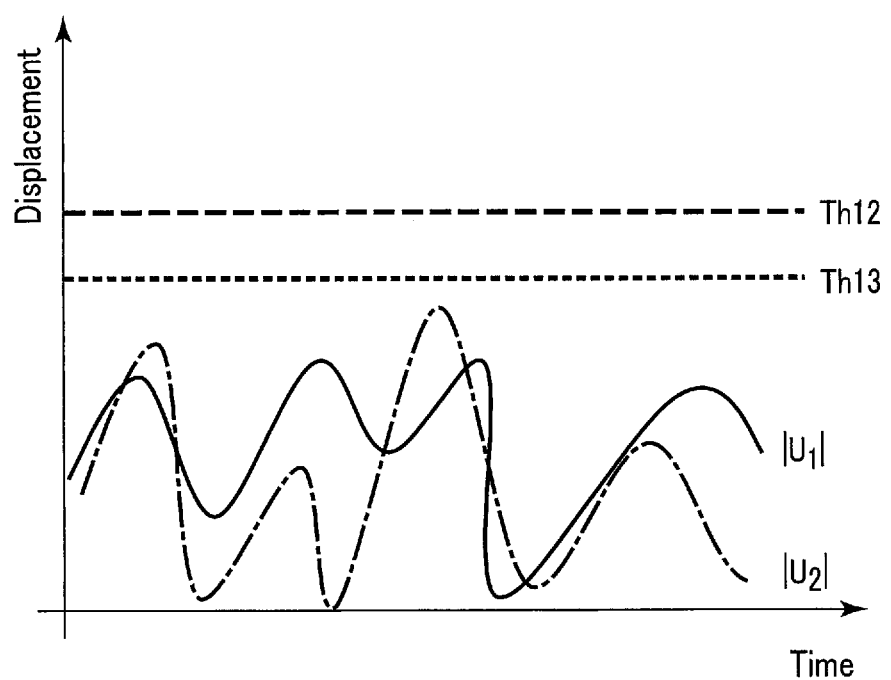
FIG. 9 is a schematic diagram for explaining magnitudes and thresholds of difference vectors acquired from FIG. 8.

FIG. 9 is a schematic diagram for explaining magnitudes and thresholds of difference vectors acquired from FIG. 8. In FIG. 9, the horizontal axis indicates the time, and the vertical axis indicates displacement. For the time-series data illustrated in FIG. 6, calculated are a first difference (displacement) vector U_1 of the position vector for the focal point Xp of the X-ray tube 121, and a second difference (displacement) vector U_2 of the position vector for the original P0 of the X-ray detector 13, at a small time interval ΔT. Hereinafter, each of difference vectors U_1 and U_2 is also referred to as difference (displacement) vectors U_i (i=1, 2). However, "i=1" indicates the focal point Xp of the X-ray tube 121, and "i=2" indicates the origin P0 of the X-ray detector 13. The processing circuitry 44 determines that the mechanical state is abnormal, in the case where one of the magnitudes |U_i| of the difference vectors U_i exceeds a threshold of a certain normal apparatus state.

Specifically, after Step ST4, at Step ST5, the processing circuitry 44 determines whether the magnitude |U_i| of the first difference vector U_1 serving as the first index has exceeded a first threshold Th12. The processing circuitry 44 also determines whether the magnitude |U_2| of the second difference vector U_2 serving as the second index has exceeded a second threshold Th13.

As a result of Step ST5, in the case where the magnitude has exceeded the first threshold or the second threshold, the processing circuitry 44 outputs "abnormality". In this operation, the processing circuitry 44 prepares a maintenance request for the abnormality (Step ST6). At Step ST6, in the case where "abnormality" is output due to the magnitude of the first difference vector exceeding the first threshold, the processing circuitry 44 calculates the first tangent motion vector of the X-ray generator 12 on the basis of the first difference vector. In the same manner, in the case where "abnormality" is output due to the magnitude of the second difference vector exceeding the second threshold, the processing circuitry 44 calculates the second tangent motion vector of the X-ray detector 13 on the basis of the second difference vector.

In addition, the processing circuitry 44 of the X-ray diagnostic apparatus 1 determines degree of freedom of motion most parallel with the first tangent motion vector and the second tangent motion vector, on the basis of the first tangent motion vector and the second tangent motion vector and the degree of freedom of motion of each of a plurality of coupling portions in the X-ray diagnostic apparatus 1. The determination function 445 also outputs "abnormality" of the coupling portion having the determined degree of freedom of motion. Thereafter, the processing circuitry 44 prepares a maintenance request for the abnormality of the coupling portion acquired as described above.

To supplement, the abnormal region of the apparatus can be specified by the following method for the mechanical abnormal state of the X-ray diagnostic apparatus 1. Herein, calculated are tangent motion vectors of the focal point Xp of the X-ray tube 121 and the origin P0 of the X-ray detector 13 in the detected abnormal state, by motion of the degree (degree of freedom of rotation of the bearing and the degree of freedom of sliding of the roller and the C-arm 14) of freedom of motion of all the coupling portions of the X-ray diagnostic apparatus 1.

$$\hat{U}_{ij}(i=1,2, j=1,2, \ldots, n)$$

j indicates the number of degree of freedom of the coupling portion. The sign "^" attached to the tangent motion vector U_ij is a hat sign. Hereinafter, the tangent motion vector U_ij with a hat sign will be expressed as "^U_ij". In the tangent motion vector U^_ij", the degree j of freedom most parallel with the difference vector U_i exists. The coupling portion having the degree j of freedom is determined to be a coupling portion in which the mechanical abnormal state occurs.

The method for detecting the degree j of freedom most parallel with the difference vector U_i in the tangent motion vectors ^U_ij is represented by the following expression (5).

$$\min_{j}\{|\hat{U}_{ij} \times U_i| < \varepsilon, i = 1 \text{ and } 2\} \qquad (5)$$

The principle of the detection method represented by the expression (5) will be described hereinafter. In the case where the difference vector U_i increases according to the abnormal state, it means occurrence of the rigid body motion with the focal point Xp of the X-ray tube 121 and the detector surface of the X-ray detector 13 serving as one unitary piece. The rigid body motion is caused by release (such as decrease in frictional force of the sliding portion and decrease in the holding power) of the degree of freedom of one of the coupling portions of the X-ray diagnostic apparatus 1. The tangent motion of the focal point Xp of the X-ray tube 121 and the origin P0 of the X-ray detector 13 according to the degree of freedom of the coupling portion is substantially parallel with the measured displacement of the focal point Xp and the origin P0. Because the measured value has an error, a certain small value ε is used for determination of parallelism.

This structure enables prediction of the abnormal part of the X-ray diagnostic apparatus 1 or the time period in which an abnormality will occur. For example, the abnormal part can be predicted as a coupling portion having the degree j of freedom. The time period in which an abnormality will occur can be predicted on the basis of at least one of the first index and the second index, in the same manner as described above. As another example, the time period in which an abnormality will occur may be predicted on the basis of the magnitude and/or change with time of the tangent motion vector ^U_ij. A proper value should be used as the time interval ΔT required for calculation of the magnitude (oscillation quantity) of oscillation, and generally a small value should be used. However, a too small value used as the time interval ΔT causes inconvenience of failure in detection of sliding of the coupling portion, and it is preferable to set a small value within the range enabling detection of sliding of the coupling portion. Prediction of the abnormal part is executed when, for example, a maintenance request is prepared at Step ST6. Prediction of the abnormal part is executed when, for example, the maintenance time period is predicted at Step ST10.

After Step ST6, the processing at each of the steps is executed as described above.

As described above, according to the third embodiment, the first motion state data is time-series data indicating oscillation of the X-ray generator caused by rattling or elastic deformation of the X-ray diagnostic apparatus during rotation imaging along time series. The second motion state data is time-series data indicating oscillation of the X-ray detector caused by rattling or elastic deformation of the X-ray diagnostic apparatus during rotation imaging along time series. This structure enables calculation of time-series data indicating oscillation caused by rattling or elastic deformation of the X-ray diagnostic apparatus during rotation imaging along time series, by calculating each of the first motion state data and the second motion state data, in addition to the advantageous effects of the first embodiment. This structure enables detailed analysis of the mechanical state of the X-ray diagnostic apparatus, in addition to the advantageous effects of the first embodiment.

In addition, according to the third embodiment, the first index is a magnitude of the first difference vector between position vectors of the X-ray generator calculated from the first motion state data for every certain time. The second index is a magnitude of the second difference vector between position vectors of the X-ray detector calculated from the second motion state data for every certain time. This structure enables acquisition of the magnitude of oscillation of the X-ray generator for every certain time, in addition to the advantageous effects described above. In the same manner, this structure enables acquisition of the magnitude of oscillation of the X-ray detector for every certain time.

In addition, according to the third embodiment, in the case where "abnormality" is output due to the magnitude of the first difference vector exceeding the first threshold, the first tangent motion vector of the X-ray generator 12 is calculated on the basis of the first difference vector. In the same manner, in the case where "abnormality" is output due to the magnitude of the second difference vector exceeding the second threshold, the second tangent motion vector of the X-ray detector 13 is calculated on the basis of the second difference vector. In addition, degree of freedom of motion most parallel with the first tangent motion vector and the second tangent motion vector is determined, on the basis of the first tangent motion vector and the second tangent motion vector and the degree of freedom of motion of each of a plurality of coupling portions in the X-ray diagnostic apparatus, and "abnormality" for the coupling portion having the determined degree of freedom of motion is output. This structure enables specification (estimation) of the coupling portion in which an abnormality has occurred in the coupling portions in the X-ray diagnostic apparatus, in addition to the advantageous effects described above.

With respect to the effects, a supplementary explanation will be made using the comparative example described above. In the comparative example, the phantom is subjected to rotation imaging to reconstruct a projection image, the characteristic value of the artifact of the reconstructed image is calculated, and the characteristic value is associated with a malfunction database prepared in advance to diagnose the mechanical state of the X-ray diagnostic apparatus. The comparative example like this cannot calculate the time-series motion/oscillation state of the apparatus from image data (CT value) of the reconstructed image, and has difficulty in specification of the malfunctional part of the apparatus unless a malfunction database associated with the characteristic values of the artifact is minutely prepared in advance. By contrast, the third embodiment enables calculation of time-series data indicating oscillation of the X-ray diagnostic apparatus during rotation imaging, as described above. In addition, the third embodiment also enables specification (estimation) of the coupling portion in which an abnormality has occurred, while removing the necessity for a malfunction database associated with the characteristic values of the artifact, as described above.

To further supplement, the third embodiment enables estimation (isolation) of the malfunction cause on the basis of the oscillation data. The third embodiment enables estimation and isolation of the malfunction cause by calculating each of an oscillation component ($\hat{U}\_ij$) of the X-ray tube and the X-ray detector serving as one unitary piece, an oscillation component ($U\_1$) of the X-ray tube alone, and an oscillation component ($U\_2$) of the X-ray detector alone. For example, the malfunction can be estimated to be caused by the structure (such as roller support) of the holder 15 in the case where the abnormality has occurred in the oscillation component of the X-ray tube and the X-ray detector serving as one unitary piece, caused by the X-ray tube (such as tube target oscillation) in the case where the abnormality has occurred in the oscillation component of the X-ray tube alone, and caused by the detector driver (such as the FPD or around and the rotation driver) in the case where the abnormality has occurred in the oscillation component of the X-ray detector alone. In addition, the third embodiment enables execution of smoother maintenance service by transmitting the estimation results of the malfunctional part included in the maintenance request to the worker in advance. The third embodiment also enables prediction of malfunction by monitoring the oscillation state of the X-ray diagnostic apparatus and recognizing change with time thereof. Specifically, this structure enables recognition of an abnormality tendency of the apparatus and planned maintenance before an abnormality occurs in the apparatus. This structure reduces a burden on the user and the maintenance worker caused by sudden malfunction.

Fourth Embodiment

The following is an explanation of an X-ray diagnostic apparatus according to a fourth embodiment.

The fourth embodiment is a specific example of the first embodiment, and has a structure in which each of the first motion state data and the second motion state data is time-series data, and each of the first index and the second index is a frequency shift quantity of spectral data acquired by subjecting the time-series data to fast Fourier transform (FFT).

Herein, the first motion state data is time-series data indicating oscillation of (the focal point Xp of the X-ray tube 121 in) the X-ray generator 12 caused by rattling or elastic deformation of the X-ray diagnostic apparatus 1 during rotation imaging along time series. The first index is a first frequency shift quantity between the first spectral data calculated by subjecting the time-series data serving as the first motion state data to fast Fourier transform (FFT) and the natural oscillation characteristic of the X-ray diagnostic apparatus 1. Examples of the natural oscillation characteristic of the X-ray diagnostic apparatus 1 include spectral data calculated by executing fast Fourier transform (FFT) for time-series data being first motion state data in the case where the mechanical state of the X-ray diagnostic apparatus 1 is normal.

The second motion state data is time-series data indicating oscillation of (the origin P0 of) the X-ray detector 13 caused by rattling or elastic deformation of the X-ray diagnostic apparatus during rotation imaging along time series. The second index is a second frequency shift quantity between the second spectral data calculated by subjecting the time-series data serving as the second motion state data to fast Fourier transform (FFT) and the natural oscillation characteristic of the X-ray diagnostic apparatus 1. Examples of the natural oscillation characteristic of the X-ray diagnostic apparatus 1 include spectral data calculated by executing fast Fourier transform (FFT) for time-series data being second motion state data in the case where the mechanical state of the X-ray diagnostic apparatus 1 is normal. The natural oscillation characteristic of the X-ray diagnostic apparatus 1 is calculated in advance and stored in the memory 51.

With this structure, the calculating function 44 of the processing circuitry 44 calculates first spectral data by subjecting the time-series data serving as the first motion state data to fast Fourier transform (FFT), in addition to the function described above. The calculating function 444 also calculates a first frequency shift quantity between the first spectral data and the natural oscillation characteristic in the memory 51. The calculating function 444 also calculates second spectral data by subjecting the time-series data serving as the second motion state data to fast Fourier transform (FFT). The calculating function 444 also calculates a second frequency shift quantity between the second spectral data and the natural oscillation characteristic in the memory 51.

In the function described above, the determination function 445 determines whether the first frequency shift quantity serving as the first index has exceeded the first threshold, and outputs "abnormality" in the case where the shift quantity has exceeded the first threshold. The determination function 445 also determines whether the second frequency shift quantity serving as the second index has exceeded the second threshold, and outputs "abnormality" in the case where the shift quantity has exceeded the second threshold.

The other constituent elements are the same as those of the first embodiment.

With the structure described above, at Step ST4 described above, the processing circuitry 44 calculates first motion state data indicating a deviation of the three-dimensional position information of the X-ray generator 12 from the standard locus position of the X-ray generator 12. The first motion state data is time-series data indicating oscillation of (the focal point Xp of the X-ray tube 121 in) the X-ray generator 12 caused by rattling or elastic deformation of the X-ray diagnostic apparatus 1 during rotation imaging along time series.

In addition, the processing circuitry 44 calculates second motion state data indicating a deviation of the three-dimensional position information of the X-ray detector 13 from the standard locus position of the X-ray detector 13. The second motion state data is time-series data indicating oscillation of (the origin P0 of) the X-ray detector 13 caused by rattling or elastic deformation of the X-ray diagnostic apparatus 1 during rotation imaging along time series.

Each of the first motion state data and the second motion state data is time-series data of oscillation information calculated from the three-dimensional spatial information, as illustrated in FIG. 8.

The processing circuitry 44 also calculates the first spectral data by subjecting the time-series data serving as the first motion state data to fast Fourier transform (FFT). The processing circuitry 44 also calculates the second spectral data by subjecting the time-series data serving as the second motion state data to fast Fourier transform (FFT).

Figure 11:
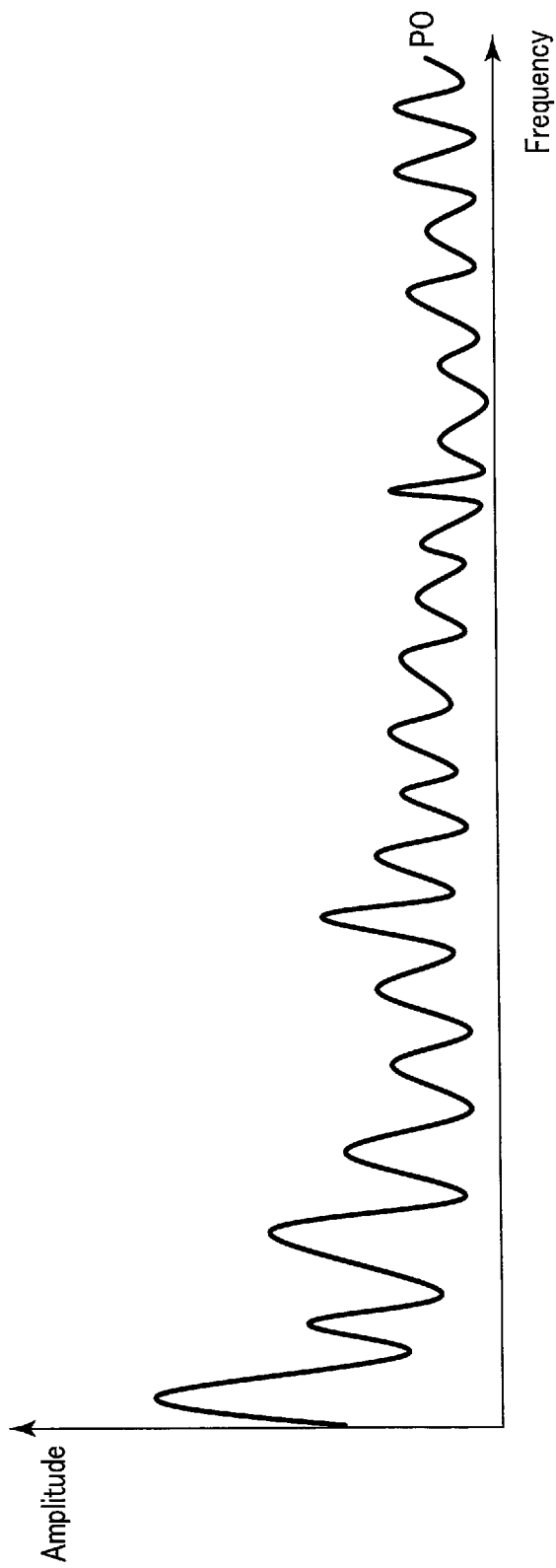
FIG. 11 is a schematic diagram for explaining a frequency spectrum relating to oscillation of the origin of the X-ray detector acquired from FIG. 8.

FIG. 10 is a schematic diagram for explaining a frequency spectrum relating to oscillation of the X-ray focal point Xp acquired from FIG. 8. FIG. 11 is a schematic diagram for explaining a frequency spectrum relating to oscillation of the origin P0 of the X-ray detector 13 acquired from FIG. 8. In FIG. 10 and FIG. 11, the horizontal axis indicates the frequency, and the vertical axis indicates the amplitude. Some peaks illustrated in each of the first spectral data of FIG. 10 and the second spectral data of FIG. 11 express natural oscillation of the X-ray diagnostic apparatus 1. In addition, according to the oscillation theory, the natural oscillation mode includes an oscillation mode of the whole X-ray diagnostic apparatus 1 and a local oscillation mode of the partial structure. The whole apparatus oscillation mode occurs in the low-frequency range, and the local oscillation mode occurs in the high-frequency range.

The processing circuitry 44 also calculates the first frequency shift quantity between the first spectral data and the natural oscillation characteristic in the memory 51. The processing circuitry 44 also calculates the second frequency shift quantity between the second spectral data and the natural oscillation characteristic in the memory 51.

Figure 12:
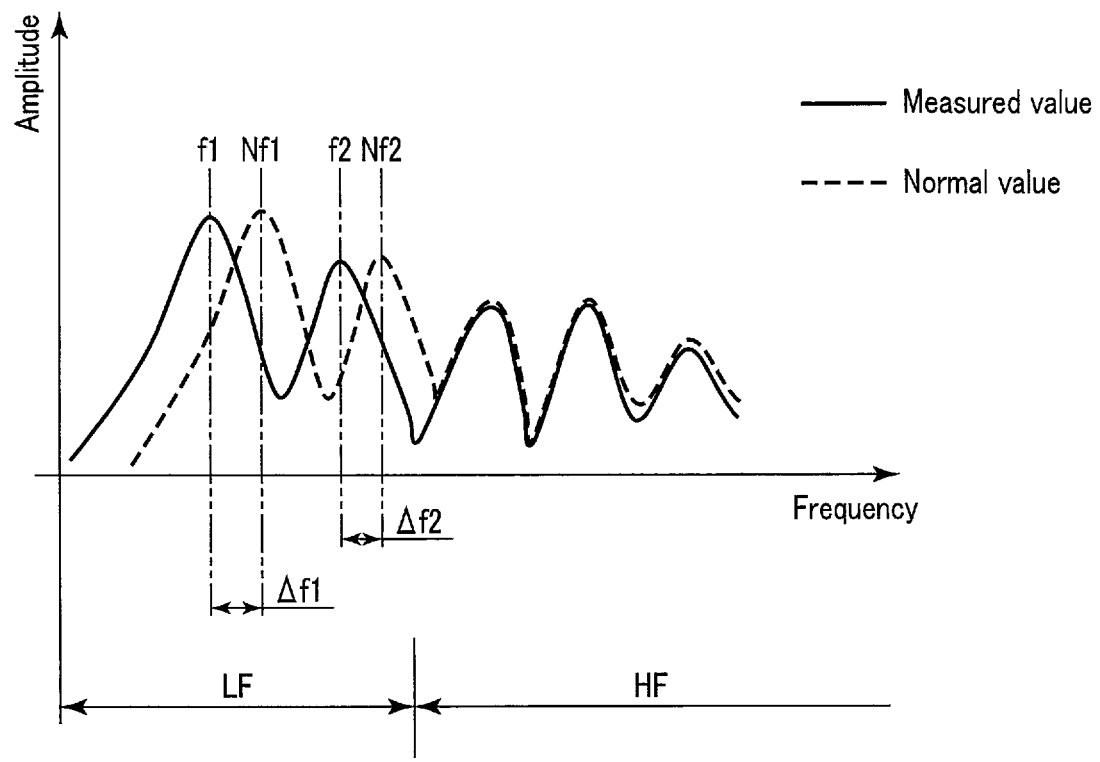
FIG. 12 is a schematic diagram for explaining a frequency shift quantity acquired from FIG. 10 or FIG. 11.

FIG. 12 is a schematic diagram for explaining a frequency shift quantity Δf acquired from FIG. 10 or FIG. 11. In FIG. 12, the horizontal axis indicates the frequency, and the vertical axis indicates the amplitude. In addition, a broken line indicates a normal value (natural oscillation characteristic of the apparatus) of the spectral data, and a solid line indicates the measured value (first spectral data or the second spectral data) of the spectral data.

In FIG. 12, the oscillation mode of the low-frequency range LF indicates the state of the bearing of the coupling portion of a large constituent element (such as the holder 15, the stand 16, and the floor turning arm 17) in the X-ray diagnostic apparatus 1. The oscillation mode of the high-frequency range HF includes a mode indicating the fixed state of the X-ray tube 121 the oscillation state of the target in the X-ray tube 121, and a mode indicating the state of the constituent element holding the X-ray detector 13.

The principle of the detection method described above will be described hereinafter. The coupling rigidity (degree of freedom other than the degree of freedom of motion) of each of coupling portions has a marked influence on the frequency of the specific natural oscillation. In this manner, relation between the natural oscillation and the coupling portion can be associated by the spectral characteristic of the X-ray diagnostic apparatus 1 measured in advance. An abnormality (such as decrease in rigidity due to insufficient fastening) of the coupling portion causes a phenomenon in which the corresponding natural oscillation frequency is shifted to the low-frequency side. In the example of FIG. 12, the natural oscillation frequencies Nf1 and Nf2 in the normal state are shifted to the natural oscillation frequencies f1 and f2 of the measured values located on the low-frequency side. Herein, the frequency shift quantity Δf1 of a certain coupling portion is "Nf1−f1". The frequency shift quantity Δf2 of another certain coupling portion is "Nf2−f2". An abnormality is detected in the case where such a frequency shift quantity Δf exceeds the threshold. In addition, the time period in which an abnormality will occur can be predicted on the basis of change with time of the frequency shift quantity. Prediction of the time period in which an abnormality will occur is executed when, for example, the maintenance time period is predicted at Step ST10.

With this structure, after Step ST4, at Step ST5, the processing circuitry 44 determines whether the first frequency shift quantity serving as the first index has exceeded the first threshold, and outputs "abnormality" in the case where the first frequency shift quantity has exceeded the first threshold. The processing circuitry 44 also determines whether the second frequency shift quantity serving as the second index has exceeded the second threshold, and outputs "abnormality" in the case where the second frequency shift quantity has exceeded the second threshold.

As a result of Step ST5, in the case where the frequency shift quantity has exceeded the first threshold or the second threshold, the processing circuitry 44 outputs "abnormality". In this operation, the processing circuitry 44 prepares a maintenance request for the abnormality (Step ST6). The abnormal part (coupling portion) can be estimated according to which natural oscillation frequency the frequency shift quantity having been exceeded the threshold is. For this reason, the estimation result of the abnormal part is preferably included in the maintenance request.

After Step ST6, the processing at each of the steps is executed as described above.

As described above, according to the fourth embodiment, the first motion state data is time-series data indicating oscillation of the X-ray generator caused by rattling or elastic deformation of the X-ray diagnostic apparatus during rotation imaging along time series. The second motion state data is time-series data indicating oscillation of the X-ray detector caused by rattling or elastic deformation of the X-ray diagnostic apparatus during rotation imaging along time series. This structure enables calculation of time-series data indicating oscillation caused by rattling or elastic deformation of the X-ray diagnostic apparatus during rotation imaging along time series, by calculating each of the first motion state data and the second motion state data, in addition to the advantageous effects of the first embodiment.

In addition, according to the fourth embodiment, the first index is first frequency shift quantity between the first spectral data calculated by subjecting the time-series data serving as the first motion state data to fast Fourier transform (FFT) and the natural oscillation characteristic of the X-ray diagnostic apparatus. The second index is a second frequency shift quantity between the second spectral data calculated by subjecting the time-series data serving as the second motion state data to fast Fourier transform (FFT) and the natural oscillation characteristic of the X-ray diagnostic apparatus. This structure enables acquisition of the frequency shift quantity of the spectral data relating to oscillation of the X-ray generator as the first index, in addition to the advantageous effects described above. In the same manner, this structure enables acquisition of the second index indicating the frequency shift quantity of the spectral data relating to oscillation of the X-ray detector.

With respect to the effects, a supplementary explanation will be made using the comparative example described above. In the comparative example, the phantom is subjected to rotation imaging to reconstruct a projection image, the characteristic value of the artifact of the reconstructed image is calculated, and the characteristic value is associated with a malfunction database prepared in advance to diagnose the mechanical state of the X-ray diagnostic apparatus. The comparative example like this cannot calculate the time-series motion/oscillation state of the apparatus from image data (CT) of the reconstructed image, and cannot analyze the frequency and/or amplitude determined from the time-series data. By contrast, the fourth embodiment enables calculation of time-series data indicating oscillation of the X-ray diagnostic apparatus during rotation imaging, as described above. The fourth embodiment also enables acquisition of the frequency shift quantity of the spectral data relating to oscillation of the X-ray generator and/or the X-ray detector, as described above.

To further supplement, the fourth embodiment enables estimation (isolation) of the malfunction cause on the basis of the oscillation data. The fourth embodiment enables estimation of the fixation and abrasion states of the coupling mechanical element (such as a bearing) of the holding unit (such as the holder 15, the stand 16, and the floor turning arm 17) of the C-arm 14 by subjecting the time-series data to spectral analysis and comparing the time-series data with the natural oscillation characteristic of the apparatus. In addition, the fourth embodiment enables prediction of malfunction by monitoring the oscillation state of the X-ray diagnostic apparatus and recognizing change with time. This structure reduces a burden on the user and the maintenance worker caused by sudden malfunction.

At least one of the embodiments described above enables diagnosis of the mechanical state of the X-ray diagnostic apparatus before an artifact occurs in the reconstructed image.

The term "processor" used in the explanation described above means a CPU (Central Processing Unit), a GPU (Graphics Processing Unit), or a circuit, such as an application specific integrated circuit (ASIC) and a programmable logic device (such as a simple programmable logic device (SPLD), a complex programmable logic device (CPLD), and field programmable gate array (FPGA)). In the case where the processor is a CPU, the processor achieves the function by reading and executing a program stored in a storage circuit. By contrast, in the case where the processor is an ASIC, the function is directly incorporated in the circuit of the processor as a logic circuit, instead of storing the program in the storage circuit. Each of the processors in the present embodiment is not limited to the case where each of the processors is formed as a single circuit, but a plurality of independent circuits may be combined to form a processor and achieve the function. In addition, the constituent elements in FIG. 1 or FIG. 6 may be integrated into a processor to achieve the functions.

While certain embodiments have been described, they have been presented by way of example only, and they are not intended to limit the scope of the inventions. These embodiments may be implemented in a variety of other forms with various omissions, substitutions, and changes without departing from the spirit of the inventions. The embodiments and their modifications are covered by the accompanying claims and their equivalents, as would fall within the scope and the gist of the inventions.

What is claimed is:
1. An X-ray diagnostic apparatus, comprising:
processing circuitry configured to execute first calculation processing of calculating three-dimensional position information of each of an X-ray generator and an X-ray detector during rotation imaging, based on projection data acquired by executing the rotation imaging for a phantom with the X-ray generator and the X-ray detector arranged rotatably around the phantom,
wherein the processing circuitry is further configured to calculate first motion state data indicating a deviation of the three-dimensional position information of the X-ray generator from a standard locus position of the X-ray generator, and calculate second motion state data indicating a deviation of the three-dimensional position information of the X-ray detector from a standard locus position of the X-ray detector.

2. The X-ray diagnostic apparatus according to claim 1, wherein
the phantom includes a plurality of beads embedded therein, and
the processing circuitry is further configured to calculate the three-dimensional position information of each of the X-ray generator and the X-ray detector, based on calibration data associating for each bead of the plurality of beads, a projection position of the bead on a detection surface of the X-ray detector and a position of the bead on a three-dimensional space of the phantom.

3. The X-ray diagnostic apparatus according to claim 1, wherein
the first motion state data is time-series data indicating an oscillation of the X-ray generator caused by a rattling or an elastic deformation of the X-ray diagnostic apparatus during the rotation imaging along time series, and
the second motion state data is time-series data indicating the oscillation of the X-ray detector caused by the rattling or the elastic deformation of the X-ray diagnostic apparatus during the rotation imaging along time series.

4. The X-ray diagnostic apparatus according to claim 1, wherein the processing circuitry is further configured to calculate a first index based on the first motion state data, and calculate a second index based on the second motion state data.

5. The X-ray diagnostic apparatus according to claim 4, wherein the processing circuitry is further configured to:
calculate the first index, which is a magnitude of a first difference vector between position vectors of the X-ray generator calculated from the first motion state data for every certain time, and
calculate the second index, which is a magnitude of a second difference vector between position vectors of the X-ray detector calculated from the second motion state data for every certain time.

6. The X-ray diagnostic apparatus according to claim 4, wherein the processing circuitry is further configured to:
calculate the first index, which is a first frequency shift quantity between first spectral data calculated by subjecting time-series data serving as the first motion state data to a fast Fourier transform (FFT) and a natural oscillation characteristic of the X-ray diagnostic apparatus, and
calculate the second index, which is a second frequency shift quantity between second spectral data calculated by subjecting time-series data serving as the second motion state data to the fast Fourier transform (FFT) and the natural oscillation characteristic of the X-ray diagnostic apparatus.

7. The X-ray diagnostic apparatus according to claim 5, wherein the processing circuitry is further configured to execute:
first determination processing of determining whether the first index has exceeded a first threshold, and outputting "abnormality" in a case where the first index has exceeded the first threshold; and
second determination processing of determining whether the second index has exceeded a second threshold, and outputting the "abnormality" in a case where the second index has exceeded the second threshold.

8. The X-ray diagnostic apparatus according to claim 7, wherein the processing circuitry is further configured to:
calculate a first tangent motion vector of the X-ray generator, based on the first difference vector, in a case where the "abnormality" is output by the first determination processing, and calculate a second tangent motion vector of the X-ray detector, based on the second difference vector, in a case where the "abnormality" is output by the second determination processing; and
determine a degree of freedom of motion most parallel with the first tangent motion vector and the second tangent motion vector, based on the first tangent motion vector and the second tangent motion vector and a degree of freedom of motion of each of a plurality of coupling portions in the X-ray diagnostic apparatus, and output the "abnormality" for the coupling portion having the determined degree of freedom of motion.

9. The X-ray diagnostic apparatus according to claim 7, wherein the processing circuitry is configured to transmit a maintenance request for the abnormality to a management terminal, in a case of outputting the "abnormality".

10. The X-ray diagnostic apparatus according to claim 4, wherein the processing circuitry is further configured to predict a time period in which an abnormality will occur in the X-ray diagnostic apparatus, based on at least one of the first index and the second index.

11. The X-ray diagnostic apparatus according to claim 10, wherein the processing circuitry is further configured to predict the time period, based on change with time of at least one of the first index and the second index.

12. A medical image processing apparatus, comprising:
a memory configured to store projection data acquired by executing rotation imaging for a phantom with an X-ray generator and an X-ray detector arranged rotatably around the phantom; and
processing circuitry configured to calculate three-dimensional position information of each of the X-ray generator and the X-ray detector during the rotation imaging, based on the projection data,
wherein the processing circuitry is further configured to calculate first motion state data indicating a deviation of the three-dimensional position information of the X-ray generator from a standard locus position of the X-ray generator, and calculate second motion state data indicating a deviation of the three-dimensional position information of the X-ray detector from a standard locus position of the X-ray detector.

13. The medical image processing apparatus according to claim 12, wherein
the phantom includes a plurality of beads embedded therein, and
the processing circuitry is further configured to calculate the three-dimensional position information of each of the X-ray generator and the X-ray detector, based on calibration data associating, for each bead of the plurality of beads, a projection position of the bead on a detection surface of the X-ray detector and a position of the bead on a three-dimensional space of the phantom.

14. The medical image processing apparatus according to claim 12, wherein the processing circuitry is further configured to calculate a first index based on the first motion state data, and calculate a second index based on the second motion state data.

15. The medical image processing apparatus according to claim 14, wherein the processing circuitry is further configured to execute:
first determination processing of determining whether the first index has exceeded a first threshold, and outputting "abnormality" in a case where the first index has exceeded the first threshold; and second determination processing of determining whether the second index has exceeded a second threshold, and outputting the "abnormality" in a case where the second index has exceeded the second threshold.

16. The medical image processing apparatus according to claim 15, wherein the processing circuitry is further configured to transmit a maintenance request for the abnormality to a management terminal, in a case of outputting the "abnormality".

* * * * *